United States Patent [19]
Domingues

[11] Patent Number: 5,571,544
[45] Date of Patent: Nov. 5, 1996

[54] SUBSTRATE-LIMITED YEAST-LEAVENED REFRIGERATED DOUGH PRODUCTS

[75] Inventor: David J. Domingues, Plymouth, Minn.

[73] Assignee: The Pillsbury Company, Minneapolis, Minn.

[21] Appl. No.: 402,939

[22] Filed: Mar. 13, 1995

Related U.S. Application Data

[60] Division of Ser. No. 87,616, Jul. 2, 1993, Pat. No. 5,492,707, which is a continuation-in-part of Ser. No. 26,927, Mar. 5, 1993, abandoned, which is a continuation-in-part of Ser. No. 732,081, Jul. 18, 1991, abandoned.

[51] Int. Cl.$^6$ ................................................... A21D 2/00
[52] U.S. Cl. ................................................ 426/62; 426/549
[58] Field of Search ........................ 426/8, 27, 62, 426/19, 549

[56] References Cited

U.S. PATENT DOCUMENTS

| | | |
|---|---|---|
| Re. 28,074 | 7/1974 | Smerak et al. . |
| 1,232,758 | 7/1917 | Blacklock . |
| 1,887,162 | 11/1932 | Lorber . |
| 2,043,139 | 6/1936 | Wille . |
| 2,333,764 | 11/1943 | Burgeson . |
| 3,096,178 | 7/1963 | Tucker . |
| 3,348,951 | 10/1967 | Tucker . |
| 3,995,066 | 11/1976 | Muys et al. . |
| 4,346,115 | 8/1982 | Clement et al. . |
| 4,374,151 | 2/1983 | Lindstrom ............................ 426/62 |
| 4,381,315 | 4/1983 | Yong et al. . |
| 4,414,228 | 11/1983 | Nourigeon ........................... 426/62 |
| 4,450,177 | 5/1984 | Larson et al. . |
| 4,500,548 | 2/1985 | Silva . |
| 4,522,832 | 6/1985 | Morrison . |
| 4,547,374 | 10/1985 | Nakatomi ............................. 426/62 |
| 4,680,182 | 7/1987 | Kawai .................................. 426/62 |
| 4,743,452 | 5/1988 | Felske ................................. 426/62 |
| 4,792,456 | 12/1988 | Katz et al. . |
| 4,966,778 | 10/1990 | Benjamin et al. . |

FOREIGN PATENT DOCUMENTS

| | | |
|---|---|---|
| 0197497 | 4/1986 | European Pat. Off. . |
| 0305071 | 8/1988 | European Pat. Off. . |
| 442575A1 | 2/1991 | European Pat. Off. . |
| 487878A1 | 10/1991 | European Pat. Off. . |
| 1051215 | 4/1955 | Germany . |
| 1007280 | 7/1961 | Germany . |
| 2740245 | 3/1978 | Germany . |
| 2757779 | 6/1978 | Germany . |
| 1587296 | 4/1981 | Germany . |
| 384114 | 12/1932 | United Kingdom . |

OTHER PUBLICATIONS

Making Mutants, by Rose and Winston, Mol. Gen. Genet. 193, 557 (1984), pp. 290, 291 and 294.
Phospholipid Breakdown in Baker's Yeast During Drying, by J. S. Harrison and W. E. Trevelyan, Dec. 21, 1963, p. 1189–1190.
Baking Science & Technology, Third Edition by E. J. Pyler, vol. 1, pp. 204–209.
A Review of Older and Some Newer Short–Time Bread Baking Studies, by P. L. Finney, The Bakers Digest Oct. 1977, pp. 81–86.
Gist–Brocades N.V. Substrate–limited doughs application.

*Primary Examiner*—Carolyn Paden
*Attorney, Agent, or Firm*—Edward Hotchkiss; Janal M. Kalis; Aleya Rahman

[57] ABSTRACT

The present invention provides refrigeratable yeast-leavened dough compositions and methods of making such doughs. The dough composition and the strain of yeast used therein are chosen to limit the total leavening action of the yeast by controlling the amount of substrate in the dough fermentable by the yeast. Dough compositions made in accordance with the invention are capable of being leavened at elevated temperatures, yet stored in a sealed container at refrigeration temperatures for extended periods of time. In one embodiment, a maltose negative yeast is used and sucrose or the like is added to the dough to serve as a fermentable substrate for the dough; this dough is suitable for storage times of up to 30 days or so. In a particularly useful embodiment which is suitable for even longer storage at refrigeration temperatures, the yeast used in the dough is substantially incapable of fermenting carbohydrates native to the dough and a predetermined quantity of a non-native carbohydrate fermentable by the yeast (e.g. galactose) is added to the dough to provide the desired amount of proofing.

6 Claims, 16 Drawing Sheets

SUBSTRATE-LIMITED YEAST-LEAVENED REFRIGERATED DOUGH PRODUCTS

This application is a division of application Ser. No. 08/087,616, filed Jul. 2, 1993, now U.S. Pat. No. 4,920,707 which is a continuation-in-part of application Ser. No. 026,927, filed Mar. 15, 1993, now abandoned, which is, in turn, a continuation-in-part of application Ser. No. 732,081, filed Jul. 18, 1991, entitled "Yeast-leavened Refrigerated Dough and Process for Making the Same", now abandoned.

FIELD OF THE INVENTION

The present invention relates to refrigeratable dough products for use in making edible baked goods. In particular, the invention provides a yeast-leavened dough which can be stored for extended periods of time at refrigeration temperatures.

BACKGROUND OF THE INVENTION

A wide range of refrigeratable dough products are currently available to consumers for producing numerous different baked products. These refrigerated doughs range from doughs for biscuits and breads to sweet rolls to cornbread products. These dough products are rather popular with consumers because they are very convenient and easy to use. Most of these products are sold in a pre-proofed state so that they can be opened to remove the dough and the dough can be baked immediately. Packaging and selling doughs in a pre-proofed state omits any necessity on the part of the consumers to carefully proof the dough for an extended period of time before baking it.

In producing refrigeratable dough products, suitably sized portions of unproofed dough are placed in individual containers. The dough is then proofed within the container, such as by holding the dough at an elevated temperature, causing the dough to expand. The dough will continue to proof until a positive internal pressure of about 15–20 psi is attained; most such containers will rapture or explode if the internal pressure of the container substantially exceeds about 40 psi. Such products are desirably capable of storage at refrigeration temperatures for at least a couple of weeks, and desirably as long as a few months, without any significant degradation of the quality of the dough or any substantial likelihood of having the containers rapture.

One disadvantage of refrigeratable dough products on the market today is that these doughs generally cannot be leavened with yeast. When yeast is used in a dough, the yeast cells will tend to continue to grow, or at least continue metabolization, even at refrigeration temperatures. The yeast therefore continues to produce carbon dioxide over the entire storage lime, unless the dough is stored in a frozen state. Although allowing yeast to ferment for the entire shelf fife of the dough may work if the dough is intended to be used immediately, extended storage (e.g. about two weeks or more) in a sealed container generally will not work because the pressure in the container will quickly build and rapture the container. If a conventional yeast-leavened dough were placed in a standard dough product container, the container may be expected to fail in no more than about two days. Additionally, continued activity of the yeast beyond the desired degree of proofing can deleteriously affect the organoleptic and rheological properties of the dough, producing unacceptable final baked products.

To date, manufacturers of refrigeratable doughs have had to replace yeast with chemical leavening agents, such as baking soda or the like. Such chemical leavening agents generally comprise a combination of a leavening acid and a leavening base, with the acid and base portions reacting to generate carbon dioxide, causing the dough to rise. One of the primary advantages of such leavening agents is that their behavior is based upon a predictable chemical reaction, permitting one to readily control the volume of carbon dioxide produced to leaven the dough. Once the chemical reaction of the leavening agents has proceeded to completion, carbon dioxide production ceases.

Although a chemically leavened dough product can be stored for extended periods of time at refrigeration temperatures, the final baked product obtained by baking such a dough is noticeably inferior to a product made with a yeast-leavened dough. Products made from yeast-leavened doughs are widely acknowledged to have superior taste, aroma and texture than those made with chemical leavening agents. Commercial dough manufacturers frequently add ingredients for the sole purpose of simulating yeast-leavened doughs. For instance, these manufacturers frequently add yeast flavoring, such as inactive pasteurized yeast cultures, to the chemically leavened dough. Even with such additives, baked products made from chemically leavened doughs lack the characteristic flavor and aroma of yeast-leavened dough and continue to exhibit relatively poor texture.

Others have attempted to solve the problems associated with storage of yeast-leavened doughs by storing the doughs at freezing temperatures rather than refrigeration temperatures. Frozen yeast-leavened doughs can yield baked goods which are noticeably better than chemically leavened refrigerated doughs. Yeast becomes inactive when frozen, thereby avoiding the problems associated with continued carbon dioxide evolution at refrigeration temperatures.

In a published European patent application (Published European Patent 0 442 575, published 21 Aug. 1991), Gist-Brocades describes a dough composition which uses a substrate limitation concept. In accordance with this disclosure, a dough is leavened with a maltose negative yeast (a yeast which cannot ferment maltose) and the dough is frozen. Gist-Brocades states that the dough may be thawed, proofed and baked anytime the same day without having to carefully monitor the proofing time. However, this dough is not designed by Gist-Brocades to be stored at refrigeration temperatures for extended periods of time, e.g. two weeks or more.

However, frozen doughs simply are not as convenient as pre-proofed refrigerated dough products. Whereas such refrigerated doughs can be baked immediately after removal from the container, frozen doughs must be allowed to thaw prior to baking. Also, since proofed dough does not survive freezing very well, frozen doughs generally must be proofed after thawing and prior to baking. This can further delay the baking of the dough. The consumer must spend more time monitoring the proofing process to avoid over-proofing the dough, making sure to place the dough in the oven for baking at the right time. Not only do such frozen doughs require more attention than do refrigerated dough products, it also requires the consumer to plan well in advance so the dough can be thawed and proofed to provide the baked goods at the desired time.

Hence, there has been a long-felt need in the industry for a yeast-leavened dough that can be stored at refrigeration temperatures for extended periods of time. To date, though, commercial producers have been unable to make and sell refrigeratable yeast-leavened doughs suitable for large-scale commercial production and extended shelf life, despite the obvious economic potential of such a product. It appears that the problems associated with the continued generation of carbon dioxide by the yeast have precluded any such product.

SUMMARY OF THE INVENTION

The present invention provides a method of making refrigeratable yeast-containing doughs and dough products made therewith. In another aspect, the invention provides a yeast-leavened refrigeratable dough composition, a dough product comprising refrigeratable dough in a container, and a baked product made from such refrigeratable dough. In accordance with the invention, a preselected strain of yeast is mixed with flour and water and, perhaps, other ingredients to form a dough. The yeast and the dough composition are chosen so that the total amount of carbohydrate or carbohydrates fermentable by the yeast in the dough is limited.

In one preferred embodiment, the yeast is substantially incapable of fermenting carbohydrates native to the flour used in the dough and a non-native carbohydrate, such as galactose, is added to the dough in an amount selected to provide the desired volume of carbon dioxide. By so doing, one may limit the maximum volume of carbon dioxide which the yeast can generate. This, in turn, prevents generation of sufficient carbon dioxide to rupture a sealed container of dough, even if the temperature of the dough is inadvertently elevated.

In another preferred embodiment, the yeast is capable of fermenting selected sugars native to the dough system which are naturally present in only limited amounts. Such sugars should be naturally present in amounts no more than, and desirably less than, that necessary to generate the volume of $CO_2$ necessary to proof the dough, with any additional sugar required to proof the dough being supplied by adding quantities of that sugar to the dough composition.

In one such embodiment, the yeast is substantially incapable of fermenting any carbohydrate native to the dough except fructose. Fructose concentration in wheats is initially on the order of less than 0.1 weight percent (wt. %). Through the action of various enzymes that can break down the disaccharide sucrose in the wheat into glucose and fructose monosaccharides, fructose concentration in the yeast may increase over time. Nonetheless, the concentration of fructose in most wheat-based dough systems is less than that necessary to generate the 100–200 ml $CO_2$ per 100 g of dough required to adequately proof the dough. Additional fructose is added to the dough to generate the desired degree of proofing.

The method may also include the additional steps of placing the resultant dough in a pressurizable container and heating the dough within the container to an elevated temperature for proofing. Once the dough in the container has been proofed, the temperature of the dough within the container is reduced to refrigeration temperatures and the dough is stored at refrigeration temperatures for an extended period of time. A method of this embodiment may further comprise the step of removing the dough from the container and baking it to produce a baked good.

BRIEF DESCRIPTION OF THE DRAWINGS

FIG. 11B is a schematic representation of the process of glycolysis, showing the reaction pathways for the utilization of various sugars in fermentation, wherein inactivated enzymes are shown with an 'x;';

FIG. 13 depicts the rate of carbon dioxide evolution for the doughs shown in FIG. 12.

DETAILED DESCRIPTION OF THE PREFERRED EMBODIMENTS

Figure 1:
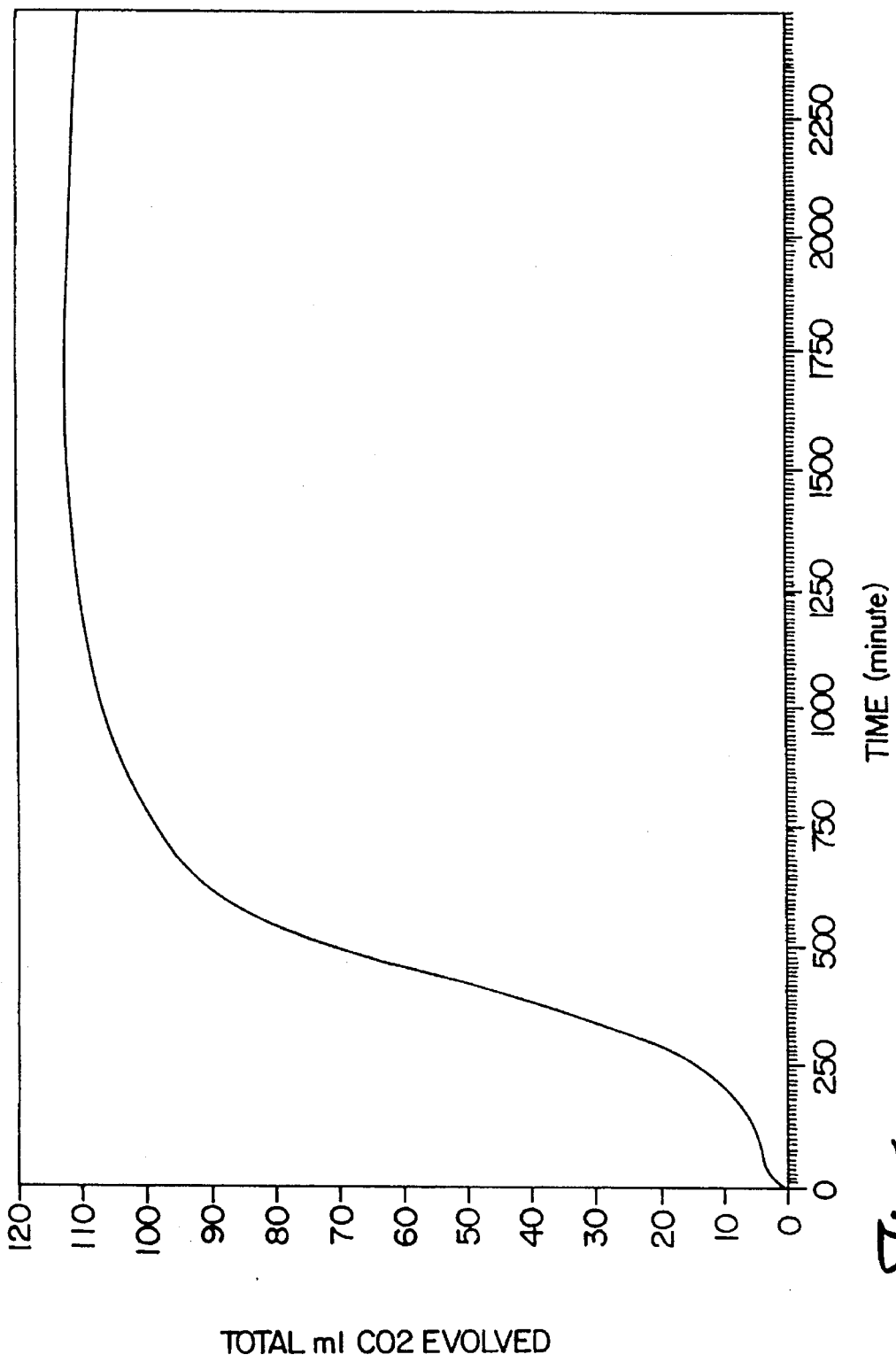
FIG. 1 is a graph showing the volume of carbon dioxide generated by MAL– yeast in a dough composition heat treated at 32° C.

In accordance with the present invention, a dough product is prepared wherein the dough composition and the yeast used therein are chosen in a manner that effectively and controllably limits the leavening action of the yeast by controlling the amount of substrate fermentable by the yeast in the dough. Strains of yeast which do not ferment certain carbohydrates are known in the art; often, two different strains of the same species of yeast are unable to ferment the same sugars. Therefore, a strain of yeast may be utilized in a dough composition which is capable of fermenting only selected sugars. By controlling the total amount of those sugars in the dough composition, the amount of fermentation can be controlled.

As explained above, even at refrigeration temperatures, most yeast will generate carbon dioxide. If the sugar substrate fermentable by the yeast is limited, carbon dioxide generation will substantially cease when the sugar is exhausted. Hence, by either allowing the yeast to metabolize the fermentable sugars in the dough for a given period of time prior to canning or controlling the sugar content of the dough, carbon dioxide generation by the yeast can be substantially terminated once a certain predetermined volume has been reached, regardless of the temperature of the dough. Accordingly, the total volume of carbon dioxide generated in the container can be prevented from reaching a level sufficient to increase internal pressure and rupture the container.

Wheat flours used in most commercial dough manufacturing operations contain about 5 weight percent (wt.%) of damaged starch. Alpha- and beta-amylases (inherent in wheat flour) convert such starch into maltose, among other sugars. Maltose and some of the other sugars produced by the action of the amylase are metabolizable by many strains of yeast.

In an earlier embodiment of the invention, a strain of yeast which did not ferment maltose, referred to as "maltose negative," or just "MAL–," was chosen. Such yeast can usually ferment other types of sugars, such as sucrose or dextrose. A number of yeasts which ferment sucrose but not maltose ("SUC+/MAL–") are commercially available, including the following strains of Saccharomyces Cerevisiae: DZ (CBS 109.90), DS 10638 (CBS 110.90), DS 16887 (CBS 111.90) V 79 (CBS 7045), and V 372 (CBS 7437). Approximately 100–200 ml of $CO_2$ per 100 grams of dough at 32° C. is usually sufficient for proofing. The total amount of fermentable sugar in the dough was adjusted in an attempt to limit the volume of carbon dioxide gas produced by fermentation of the entire fermentable sugar supply.

EXAMPLE 1

In order to test a dough product leavened with a MAL– yeast as a means of providing a refrigeratable yeast-leavened dough composition, water and a MAL– yeast were slurried together to produce a total combined weight of approximately 194 grams. The slurry contained 189 grams of water and 4.8 grams of the yeast. The yeast used in making the slurry was a MAL– strain of yeast which was obtained in a paste form. The paste was mixed with water at room temperature (approximately 23° C.) and allowed to sit at room temperature for about 10–15 minutes.

To this slurry was added 261.74 grams of flour, 18.77 grams of wheat gluten pre-blend, 3.60 grams of salt and 1.20 grams of dextrose. The wheat gluten pre-blend was 75 wt. % vital wheat gluten, 21.9 wt. % hard, high gluten, enriched ingredient flour, 2.50 wt. % xanthan gum, and 0.616 wt. % azodicarbonamide premix. The resulting dough composition therefore contained 54.53 wt. % flour, 3.91 wt. % gluten pre-blend, 0.75 wt. % salt, and 0.25 wt. % dextrose, with a final concentration of 1.00 wt. % MAL– yeast.

The dough composition was mixed in a Farinograph™ mixing bowl at 60 rpm for 4.5 minutes. Immediately after mixing, a 50-gram sample of the dough composition was placed into a Risograph™ testing machine. The Risograph is commercially available from Sheldon Manufacturing, Inc. for detecting the volume of gas, e.g. carbon dioxide, generated by a sample and the rate at which the gas is generated.

Figure 2:
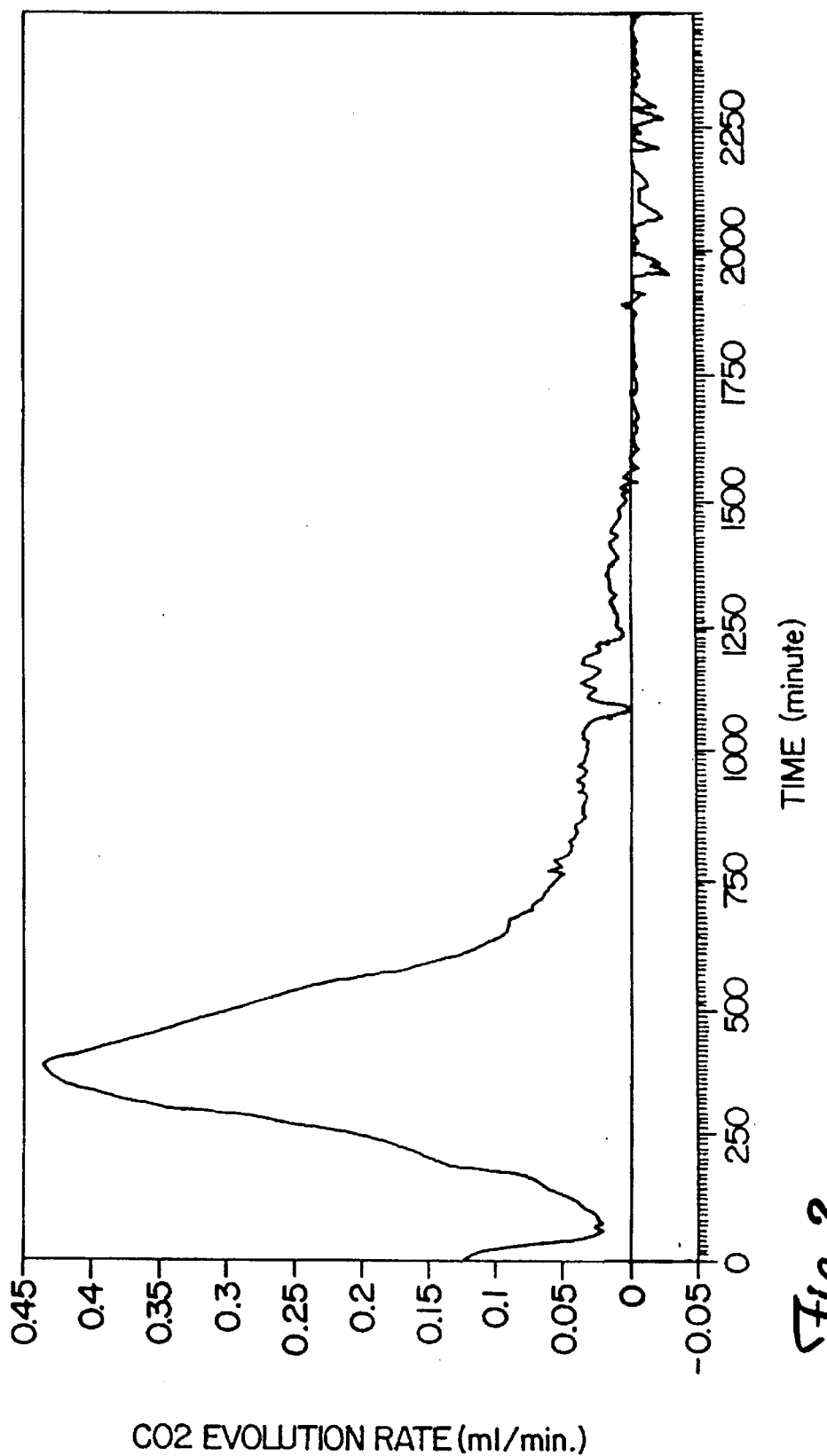
FIG. 2 shows the rate of carbon dioxide evolution for the dough shown in FIG. 1.

FIGS. 1 and 2 show the data collected in the Risograph for the sample. Of particular interest, the dough appeared to effectively cease producing carbon dioxide after about 1500 minutes at 32° C. Dough products made with this dough by placing the dough in standard spirally wound refrigeratable dough containers were found to maintain acceptable internal pressures, e.g., below about 20 psi, for about 25 days. However, carbon dioxide once again began to be generated by the dough after about 25 days. This renewed activity of the yeast in the dough was projected to be sufficient to generate enough carbon dioxide to cause all of the containers of Example 1 to rupture after about 50–55 days.

It has not been conclusively determined why the yeast became active after apparently substantially ceasing fermentation. However, one factor which is believed to have contributed to the generation of additional carbon dioxide, and subsequent failure of the containers, is a change in the carbohydrates present in the dough. As noted above, alpha- and beta-amylases, which are inherent in wheat flours, act on carbohydrates present in the dough, and particularly in the flour. Over lime, these amylases break down oligosaccharides which are not fermentable by the yeast, such as maltose and maltotriose, into sugars which can be fermented by the yeast. Accordingly, it is anticipated that, even if the yeast used in such a dough composition were truly maltose negative, the changing carbohydrate profile of the dough may present sugars which are fermentable by the yeast. Accordingly, the dough could continue to generate carbon dioxide and cause containers to rupture.

Thus, a dough product made with a MAL– yeast and a limited amount of initial maltose in the composition can be useful for storage at refrigeration temperatures for shorter periods of time, with a storage period on the order of about 30 days or less. If such dough products were stored for significantly longer periods of time, it is likely that the containers would begin to fail. Although a shelf life of 30 days may be suitable for some applications, current refrigerated dough products are expected to have an anticipated shelf life at refrigeration temperatures of 90 days or more. Accordingly, this MAL– embodiment of the invention may have only limited commercial application, with commercial use being limited to institutional markets, such as in-store bakeries and the like, where an anticipated shelf life of 30 days may nonetheless be considered acceptable.

In accordance with a preferred embodiment of the present invention suitable for significantly longer storage at refrigeration temperatures, the strain (or strains) of yeast used in the dough are substantially incapable of fermenting carbohydrates which are native to the flour. In the case of doughs using wheat flour, these native carbohydrates include sugars such as maltose, sucrose, glucose, fructose and various oligosaccharides made up of these sugars. If other flours were to be used, of course, there may be some variation in the sugars native to such a flour.

Use of such a yeast has been found to effectively prevent the yeast from fermenting any carbohydrates in the dough which are either initially present in the dough composition or result from the action of alpha- and beta-amylases on the carbohydrates initially present in the dough. A predetermined quantity of a non-native carbohydrate which is fermentable by the yeast may be added to the dough to provide the desired amount of proofing. Once that substrate is consumed, the fermentation activity of the yeast appears to substantially cease, preventing further carbon dioxide generation and avoiding overfermentation of the dough. It has been found that dough compositions in accordance with this embodiment of the invention can be used to make dough products which can be stored for periods of time in excess of 90 days without rupturing or exploding.

The non-native carbohydrate which can be fermented by the yeast strain in the present dough can be virtually any carbohydrate which does not naturally occur in the flour. This carbohydrate is preferably a sugar or an oligosaccharide, though. For instance, the fermentable, non-native sugar may be galactose or lactose, a disaccharide of glucose and galactose.

In one particularly preferred embodiment, the yeast is capable of fermenting galactose, which is not native to wheat flours, but is substantially unable to ferment any sugars which are native to wheat flour; this yeast is referred to below as a "galactose positive" or "GAL+" yeast. This GAL+ yeast is mixed with flour, water and galactose to form a dough. The amount of galactose in the dough is selected to limit the activity of the yeast so that the dough is proofed no more than the desired degree. As noted above, in most circumstances about 100–200 ml of carbon dioxide per 100 grams of dough at 32° C. is sufficient to proof the dough. Accordingly, the weight percentage of galactose in the dough composition should be chosen to generate no more than approximately 200 ml of carbon dioxide per 100 grams of dough at 32° C. The amount of galactose necessary to generate this volume of carbon dioxide will have to be determined on a case-by-case basis as the amount may vary for different strains of yeast.

Given the present disclosure, it will be well within the ability of those skilled in the art to make yeasts which are substantially incapable of fermenting carbohydrates native to flour but capable of fermenting other carbohydrates. Such yeasts can be made through standard methods of crossing yeast strains, isolating suitable strains having the desired properties and the like. These types of common techniques are described, for example, by Sherman et al. in *Methods in Yeast Genetics*, the teachings of which are incorporated herein by reference. Of particular interest in the Sherman et al. publication is Section III, entitled "Making Mutants", which appears on pages 273–369 of this reference.

Lobo and Maitra teach a method of rendering a hexokinase negative strain of *S. Cerevisiae* glucokinase negative (i.e., a method for making a GAL+ yeast strain) using standard techniques in "Physiological Role of Glucose-Phosphorylating Enzymes in Saccharomyces Cerevisiae," Archives of Biochemistry and Biophysics 182, 639–645 (1977), the teachings of which are incorporated herein by reference. In accordance with that method, the hexokinase negative strain was mutagenized with N-methyl-N'-nitro-N-nitrosoguanidine in yeast extract-peptone medium (YEP) containing 50 mM glucose-free galactose, and a glucokinase-negative mutant was isolated by replica plating from a YEP galactose plate to a YEP glucose plate as a glucose-negative colony. The genotype of the mutuant, determined by independent genetic analysis, was hxk1 hxk2 glk1, where hxk1 and hxk2 stand for genes coding P1 and P2 hexokinases respectively, and glk1 for the genetic determinant for glucokinase synthesis.

Although Lobo and Maitra teach one suitable method of making a yeast for use in accordance with the present invention, others methods will be apparent to those skilled in the art. Those in the art will also realize that other strains of yeast which are substantially incapable of fermenting carbohydrates native to a particular flour but capable of fermenting non-native carbohydrates other than galactose can be made by known methods.

EXAMPLE 2

In order to test the ability of a GAL+ yeast to ferment carbohydrates which are native to a common dough system, a dough composition containing GAL+ yeast was prepared. This dough formula included 870.75 g (58.05 wt. %) wheat flour, 529.80 g (35.32 wt. %), water, 58.20 g (3.88 wt. %) of the wheat gluten preblend used in Example 1, 11.25 g (0.75 wt. %) salt and 28.50 (2.00 wt. %) yeast. The yeast used in this experiment was a GAL+ strain of *Saccharomyces Cerevisiae* designated as D308.3; this yeast was of the genotype α hxk1 hxk2 glk1 ade1 trp1 his2 met4. This yeast is available to the public from the Yeast Genetic Stock Center at the Donner Laboratory in the Department of Molecular and Cell Biology of the University of California, Berkeley (YGSC); in the Seventh Edition of the catalog of the YGSC dated Mar. 15, 1991, this strain of yeast was listed under stock no. D308.3. This yeast strain was also deposited with the American Type Culture Collection of 12301 Parklawn Drive, Rockville, Md.20852, USA (ATCC), on 5 Mar. 1993, under number ATCC 74211.

Isolated colonies of the D308.3 yeast from solid galactose agar plates were used to inoculate six 50 ml culture flasks containing liquid yeast extract-peptone ("YEP") and galactose. The samples were incubated for approximately 20 hours at about 30° C. and then used to inoculate six one-liter flask samples, which also contained YEP and galactose. These 1 L flasks were incubated for about 24 hours at 30° C., followed by incubation at about 240C. for approximately 20 hours.

This yeast was then harvested using a GSA rotor, which is commercially available from Sorval Instruments. Sample containers for use with the GSA rotor were filled so that the total weight of the sample, lid and container was about 300 g. The sample container was spun at 2500 rpm for 20 minutes, and the supernatant fluid was immediately decanted. Enough distilled water to raise the total weight of the sample, lid and container to 300 g was added to the sample container, and the container was swirled to bring the yeast pellet back into suspension. This sample container was then spun at 2500 rpm for 20 minutes again, and the supernatant fluid was again decanted.

The washed yeast paste and water were combined to form a slurry. This slurry was mixed with the other ingredients in a table-top Hobart mixer. The dough was mixed at speed 1 for 30 seconds, followed by mixing at speed 2 for between about 4 and about 5 minutes. Two 100 g samples (A1 and A2 in FIGS. 3 and 4) and two 50 g samples (A3 and A4 in FIGS. 3 and 4) were placed in the Risograph testing machine used in connection with Example 1 above. The samples were incubated at about 30° C. for about 17 hours (1,0012} minutes). The results of this Risograph testing are shown in FIGS. 3 and 4.

Figure 3:
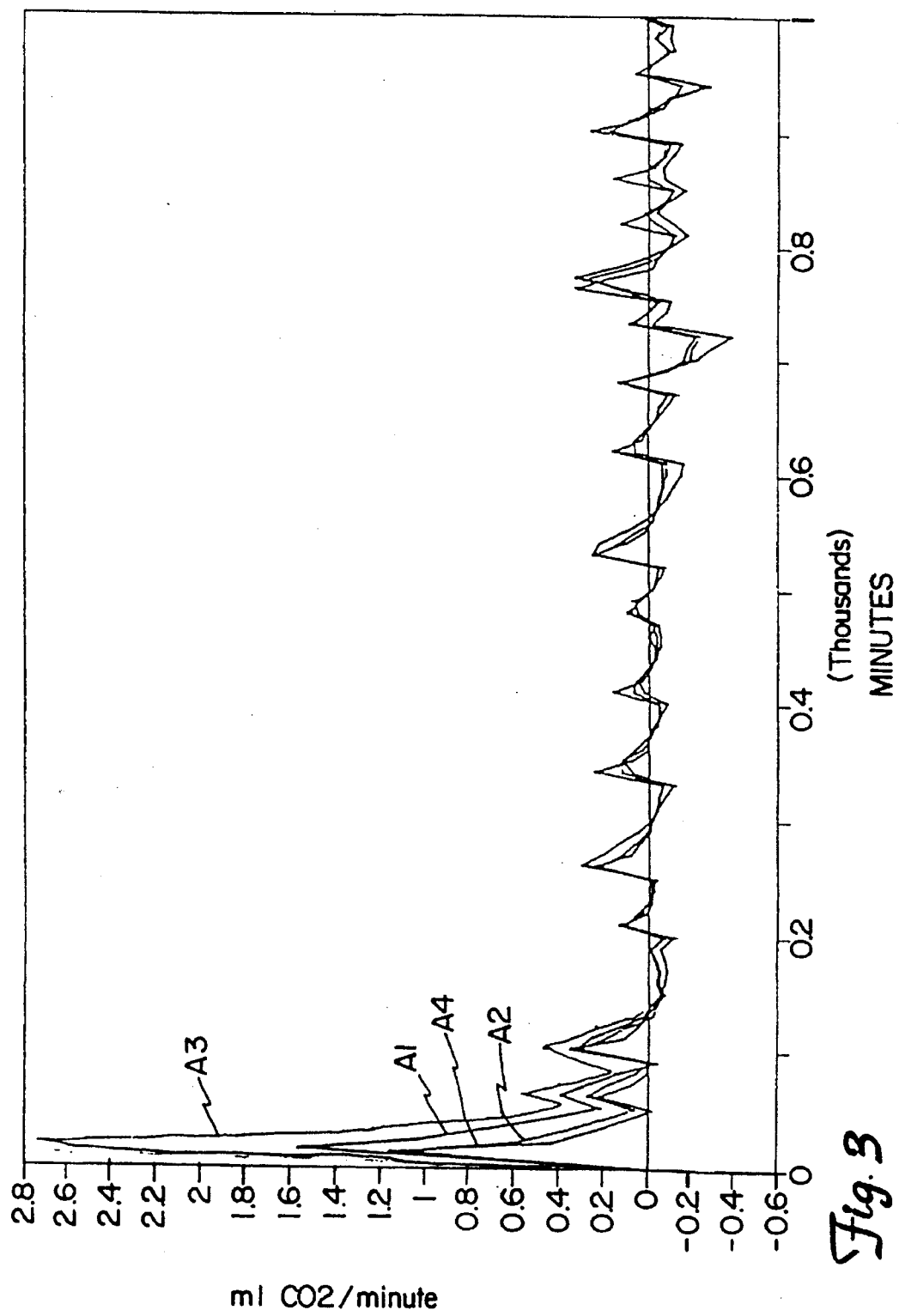
FIG. 3 is a graph depicting the rate of carbon dioxide generation over time for a GAL+ yeast in a dough composition held at 30° C.

As can be seen in FIG. 3, carbon dioxide was generated fairly rapidly in all of these samples for the first 40–50 minutes, after which the rate of evolution tapered off to about zero. Although the rate of carbon dioxide generation appears to have fluctuated between slight positive and negative rams, it appears as though the samples generated very little or no carbon dioxide between about 120 minutes after incubation began and the end of the experiment.

Figure 4:
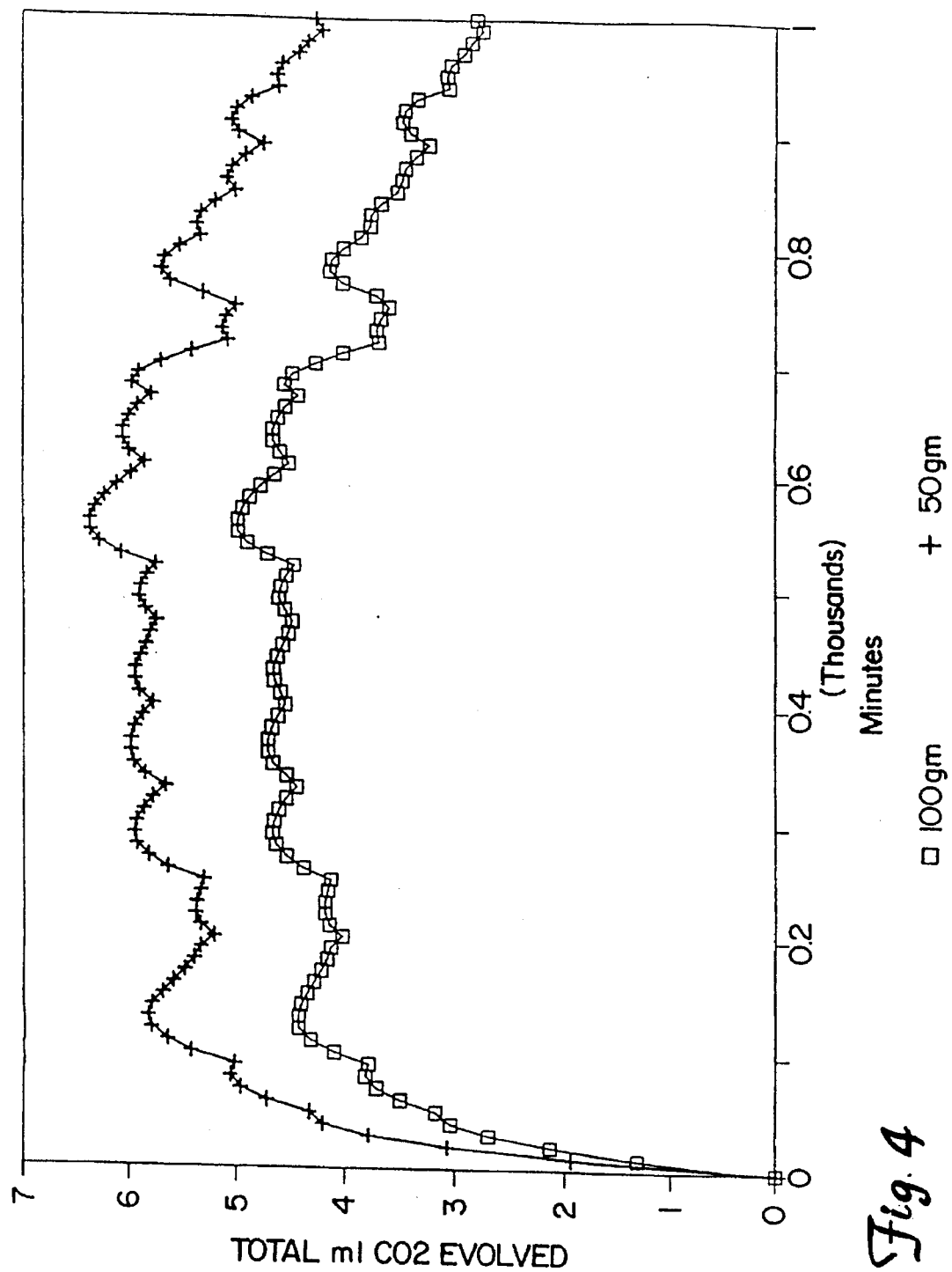
FIG. 4 shows the total volume of carbon dioxide generated in the sample of FIG. 3.

Furthermore, although the rate of carbon dioxide generation was noticeable at the beginning of the experiment, it should be noted that the total volume of carbon dioxide generated in this sample was no more than about 7 ml; this result is best seen in FIG. 4. As noted above, in order to adequately proof dough, between about 100 and about 200 ml of carbon dioxide/100 g of dough is generally considered to be necessary. The volume of carbon dioxide generated in these galactose-free samples, though, fell well below those limits. The indication that about 7 ml of gas was generated in these samples may actually be attributable primarily, if not entirely, to an expansion of the headspace in the Risograph sample containers when the containers were heated for incubation. In other words, it appears likely that no appreciable carbon dioxide was generated by the dough samples in this experiment.

Accordingly, the D308.3 yeast used in this Example can be said to be substantially incapable of fermenting, or otherwise metabolizing, the carbohydrates native to this dough system. Hence, it is believed that the D308.3 strain of yeast can be accurately referred to as GAL+, as that term is used herein, and this yeast provides one example of a yeast suitable for use in the present invention. As noted above, though, one of ordinary skill in the art could make other GAL+ yeasts, as well as other yeasts which are capable of fermenting only carbohydrates not native to the flour in the dough, in light of the present disclosure.

EXAMPLE 3

In order to test the responsiveness of the GAL+ yeast used in Example 2, four different dough compositions, with varying non-native carbohydrates, were prepared. Each of the four doughs included 290.25 g of flour, 176.60 g of water, 3.50 g of salt and 12.00 g of the D308.3 GAL+ yeast used in Example 1. The formulas of the four different doughs varied in the nature of the other ingredients which were added. In a control sample, no other ingredients were added; in a second sample, 5.00 g of galactose was included; in a third sample, 10.00 g of lactose was provided; and the final sample included 20.00 g of non-fat dry milk (NFDM), which is used as a flavoring ingredient in some doughs and typically contains some lactose and may contain slight amounts of galactose.

Figure 5:
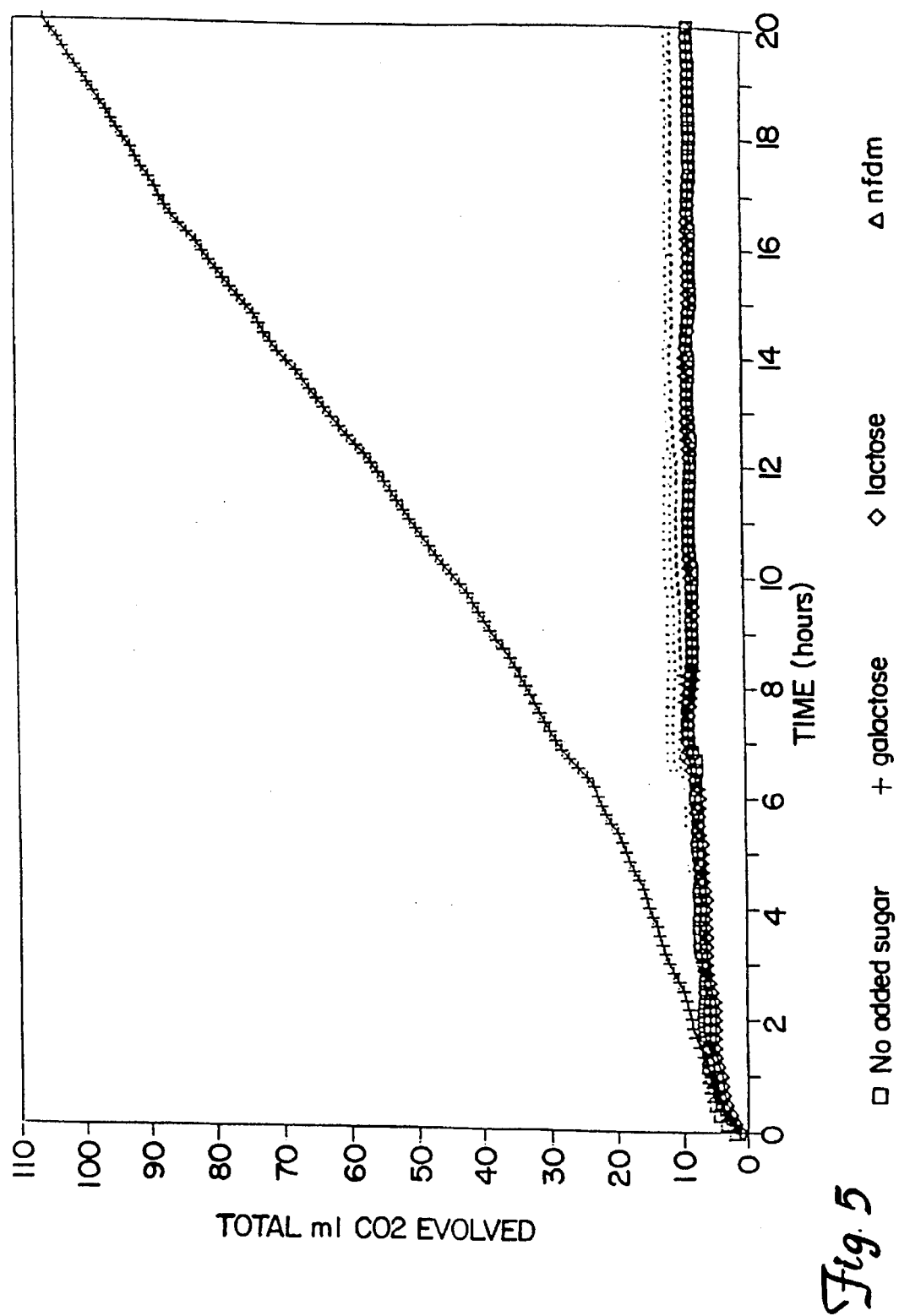
FIG. 5 is a graph showing the total volume of carbon dioxide generated by four dough compositions differing in the nature of non-native carbohydrates added to the dough.
Figure 6:
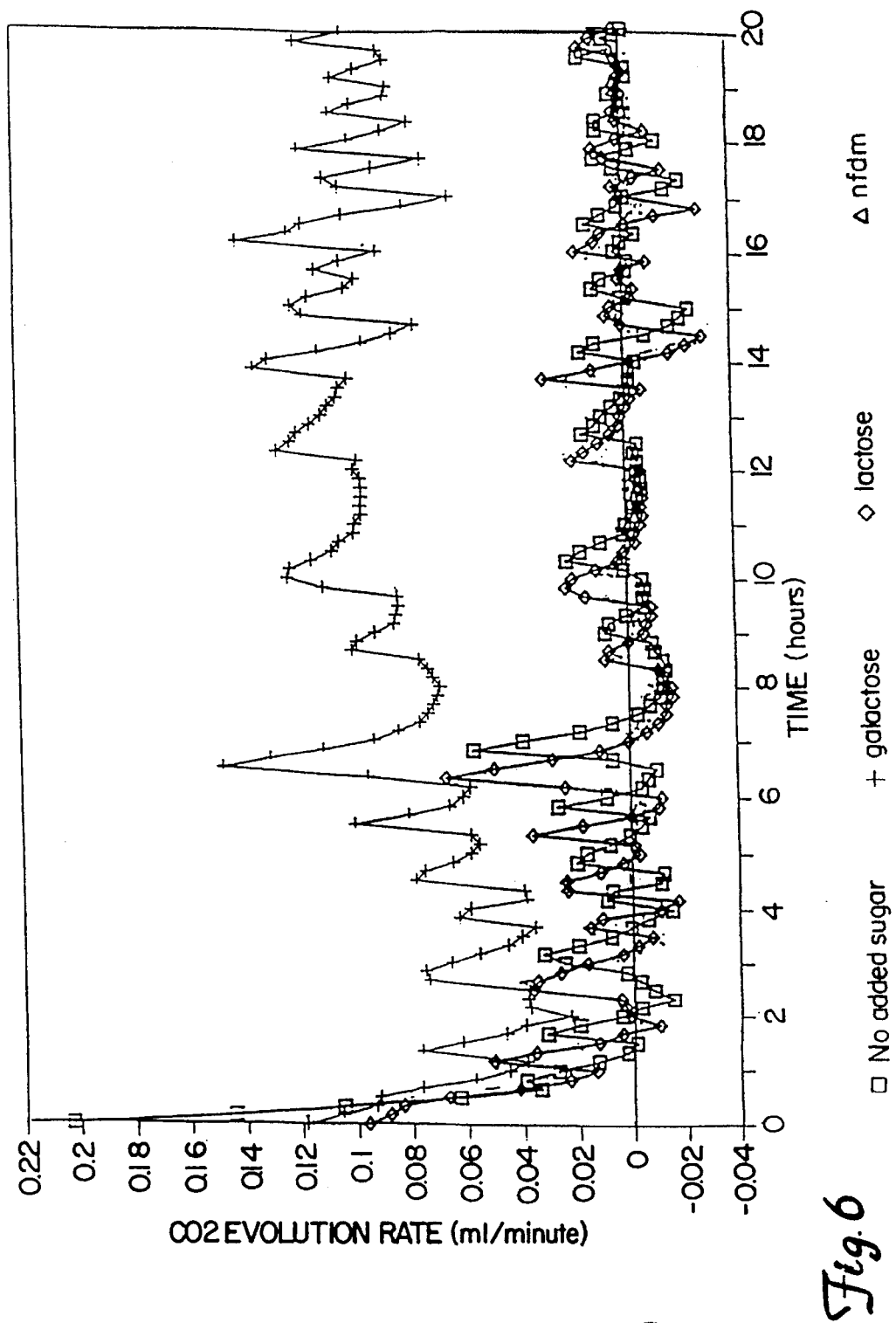
FIG. 6 depicts the rate of carbon dioxide evolution for the doughs shown in FIG. 5.

Yeast paste was grown and harvested in substantially the same manner as set forth in connection with Example 2. For each of the samples, the washed yeast was slurried with the water, and this slurry was added to the other ingredients in a table-top Hobart mixer. Each sample was then mixed at speed 1 for about 30 seconds, followed by mixing at speed 2 for about 4 minutes. Two 100 g samples of each of the dough compositions were placed into Risograph sample jars immediately after mixing and held in the Risograph at about 28° C. for approximately 20 hours. FIGS. 5 and 6 show the total volume of carbon dioxide evolved and the ram of carbon dioxide evolution, respectively, for each of the samples.

As can be seen from FIGS. 5 and 6, only the dough composition which included galactose generated appreciable volumes of carbon dioxide. The control sample, the lactose-containing sample and the sample with the NFDM all generated less than about 10 ml of carbon dioxide over a period of about 20 hours. Furthermore, essentially all of the carbon dioxide generation measured for the non-galactose doughs was generated in the first one to two hours of incubation. This slight change in gas volume in the Risograph sample jars may be wholly attributable due to thermal expansion of the headspace in the sample jars, as explained above. Accordingly, the samples which did not contain non-native galactose quite likely did not generate any significant amount of carbon dioxide during the course of this test.

The results of this experiment show that the D308.3 yeast can metabolize galactose but it is substantially incapable of fermenting any carbohydrates which are native to flour of the dough composition. It also appears that this yeast is substantially incapable of fermenting either "straight" lactose or lactose in non-fat dry milk. During the course of this experiment, the galactose-containing dough appears to continue to generate carbon dioxide, indicating that not all of the galactose was used. Furthermore, at the end of the 20-hour incubation, the galactose dough had generated slightly more than 100 ml of carbon dioxide, with carbon dioxide generation appearing to continue beyond the end of the experiment.

The dough containing galactose was about 1.0 wt. % galactose (5,00 g galactose/487.35 g total dough). Based on the results of this experiment, it appears that about 1 wt. % galactose is more than adequate to generate the desired 100–200 ml of carbon dioxide per 100 g of dough. Additional experimentation using standard, spirally wound composite containers of about 250 cc capacity, such as are commonly used in packaging commercial refrigerated doughs, has established that about. 0.5 wt. % to about 1.0 wt. % galactose is sufficient to generate enough carbon dioxide to reach an internal pressure of about 10–20 psi. Accordingly, in making a refrigeratable dough product of the invention, the dough placed in the container optimally includes between about 0.5 wt. % and about 1.0 wt. % galactose.

EXAMPLE 4

The D308.3 yeast was added to a chemically-leavened dough product in order to see if the presence of the GAL+ yeast affected the integrity of the container if no galactose was added to the dough. Two batches of a dough con mining the D308.3 yeast and two separate batches of chemically leavened dough were prepared. The chemically leavened doughs had the following formula: about 1590 g (56 wt. %) flour, 947 g (33.43 wt. %) water, 110 g (3.9 wt. %) of the wheat gluten pre-blend of Example 1, 89.2 g (3.15 wt. %) of yeast flavorings, 42.5 g (1.5 wt. %) glucono delta lactone (GDL), 32.0 g (1.13 wt. %) baking soda, and 21.3 g (0.75 wt. %) salt. The two batches of dough containing yeast had a very similar formula, with the approximately 947 g (33.4 wt. %) of water being replaced with about 890 g (31.4 wt. %) of water and about 56.7 g (2.00 wt. %) D308.3 yeast.

The water in each of these batches was first mixed with the flavoring ingredients before being charged with the flour and gluten pre-blend into a McDuffy mixing bowl. In the batches containing yeast, the yeast was slurried with the water before the flavoring ingredients were added to this slurry. The ingredients were mixed at speed 1 for about 30 seconds, followed by mixing at speed 2 for about 5 minutes. The salt and the leavening agents (GDL and soda) were then added to this dough and the mixture was mixed at speed 1 for approximately 30 seconds and at speed 2 for about 2.5 minutes.

Each batch of dough was sheeted to a thickness of about ¼ inch (about 0.64 cm) and rolled into a long "log" of dough. Each log of dough was divided into a series of samples weighing about 210 g and each sample was sealed into a standard, spirally wound composite can having a 250 cc capacity. These dough products were then proofed at about 32°–35° C. until an internal pressure of about 10–15 psi in the containers was reached. After this proofing, the dough products were transferred to refrigerated storage at about 4° C.

Figure 7:
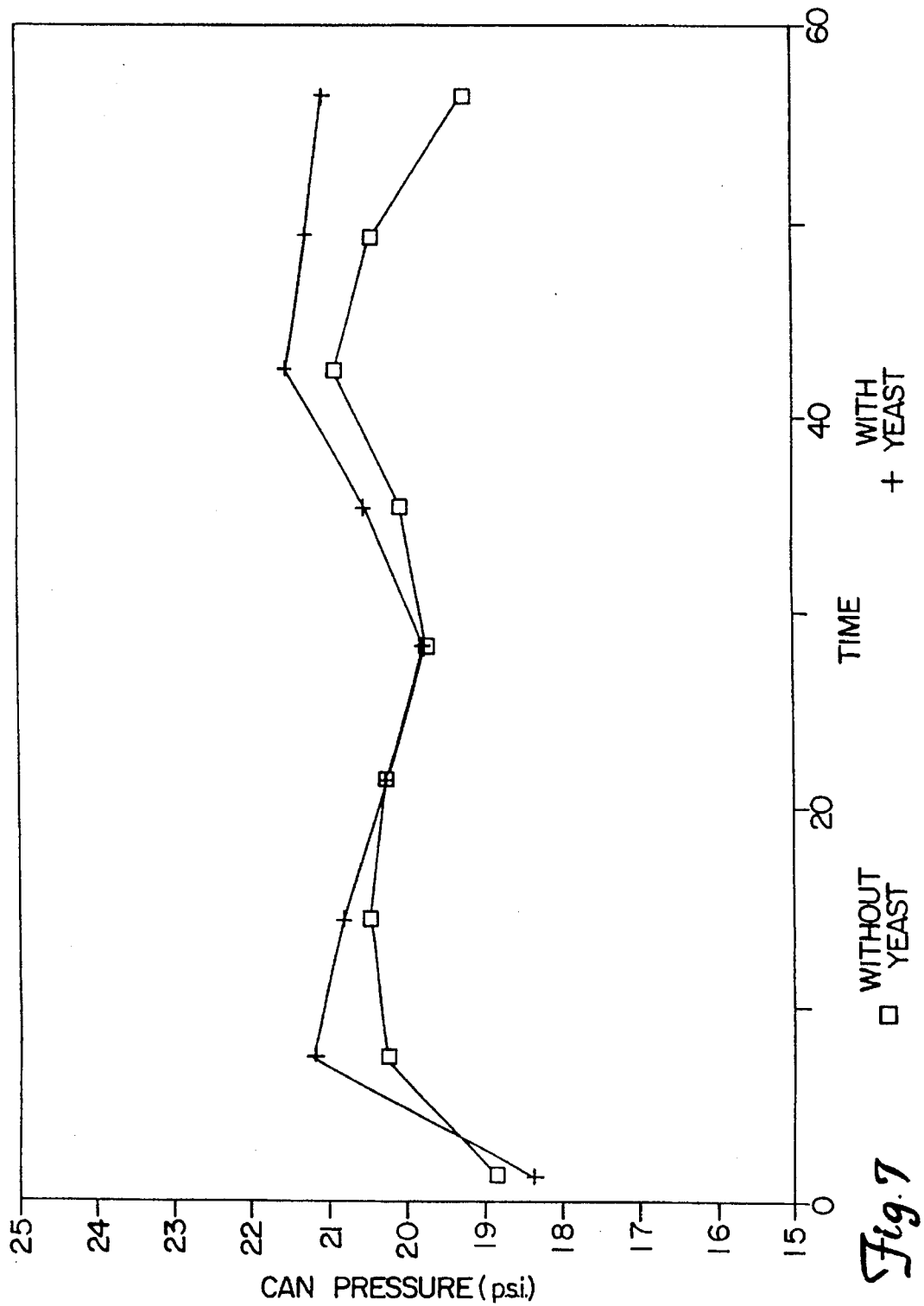
FIG. 7 plots measured can pressure over time for two chemically leavened doughs, one containing a GAL+ yeast, the other without.

FIG. 7 plots the measured can pressure, i.e., the internal pressure of the container, as a function of time. As can be seen in FIG. 7, there does not appear to be any significant difference between the pressure in the dough product containing the standard chemically leavened dough and the dough product containing the chemically leavened dough with the GAL+ yeast.

A variety of other physical measurements were made on the different samples to compare the standard chemically leavened dough with the yeast-doped dough. Among the physical measurements compared were water retention, pH, and sugar content. Samples of the doughs were also baked at approximately 375° F. (163° C.) for about 20 minutes. The specific volume, as well as the appearance, aroma and other sensory properties, of the resulting baked goods were compared. Aside from a slightly lower specific volume for the sample containing the GAL+ yeast, there did not appear to be any significant differences between these two dough compositions.

EXAMPLE 5

The relationship between galactose content of the dough and the resultant internal pressures of dough products containing dough in accordance with the invention was tested. Four different batches were prepared, with the batches differing only in the amount of galactose added. Each dough composition contained about 870.75 g (58.05 wt. %) wheat flour, 529.80 g (35.32 wt. %), water, 58.20 g (3.88 wt. %) of the wheat gluten preblend used in Example 1, 11.25 g (0.75 wt. %) salt and 28.50 g (2.00 wt. %) D308.3 yeast. Additionally, one batch contained about 5.92 g (0.5 wt. %) galactose, another contained about 7.40 g (0.63 wt. %) galactose, a third contained about 8.87 g (0.75 wt. %) galactose, and the final batch contained about 11.83 g (1.00 wt. %) galactose.

The D308.3 yeast was grown and harvested in substantially the same manner as that detailed above in Example 2. In forming batches of dough containing the 0.5 wt. % and 1.0 wt. % galactose, the yeast paste was then mixed with the water and the galactose in a 1 L culture flask and incubated in the flask for about 1 hour at about 30° C. while the flask was agitated. This slurry was then added to a McDuffy mixing bowl and mixed with the other ingredients at speed 1 for about 30 seconds, followed by mixing at speed 2 for about 7 minutes. The 0.63 wt. % and 0.75 wt. % galactose batches were prepared slightly differently in that the yeast, water and galactose were not incubated prior to being mixed with the other ingredients. Instead, these three ingredients were slurried in a table-top Hobart and were mixed at speed 2 for only about 4 minutes with a dough hook.

After the doughs were mixed, two 50-gram samples from each batch of dough were placed in Risograph sample jars and incubated in the Risograph at about 28°–30° C. The dough was then rolled, divided into 2 10-gram samples, and packaged in a standard refrigeratable dough container, as outlined above in Example 4. The resultant dough product was incubated at about 35° C. for about three hours and subsequently stored at about 4° C.

Figure 8:
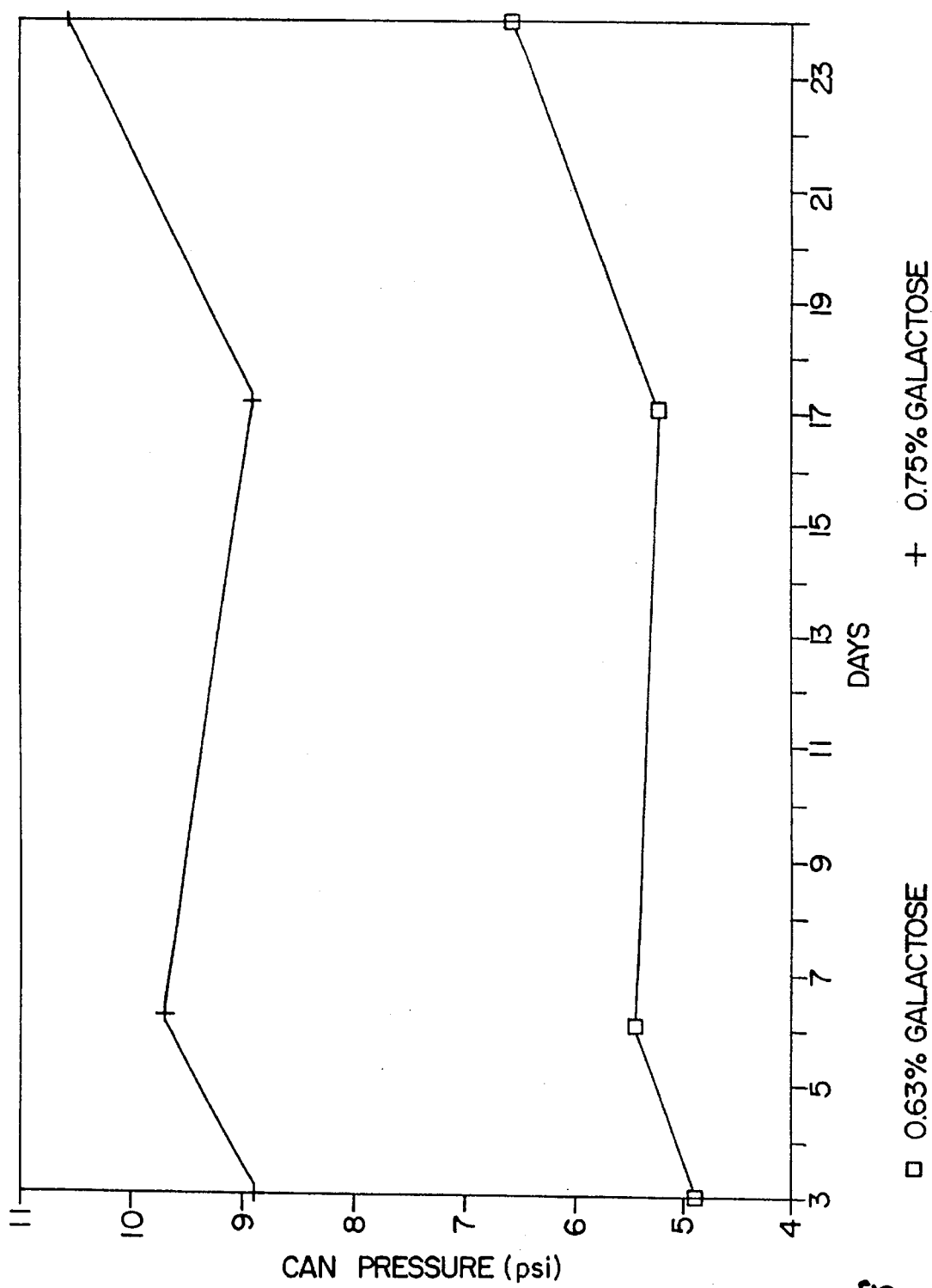
FIGS. 8 and 9 show can pressure over time for three dough samples having different mounts of non-native sugar incorporated in their composition.
Figure 9:
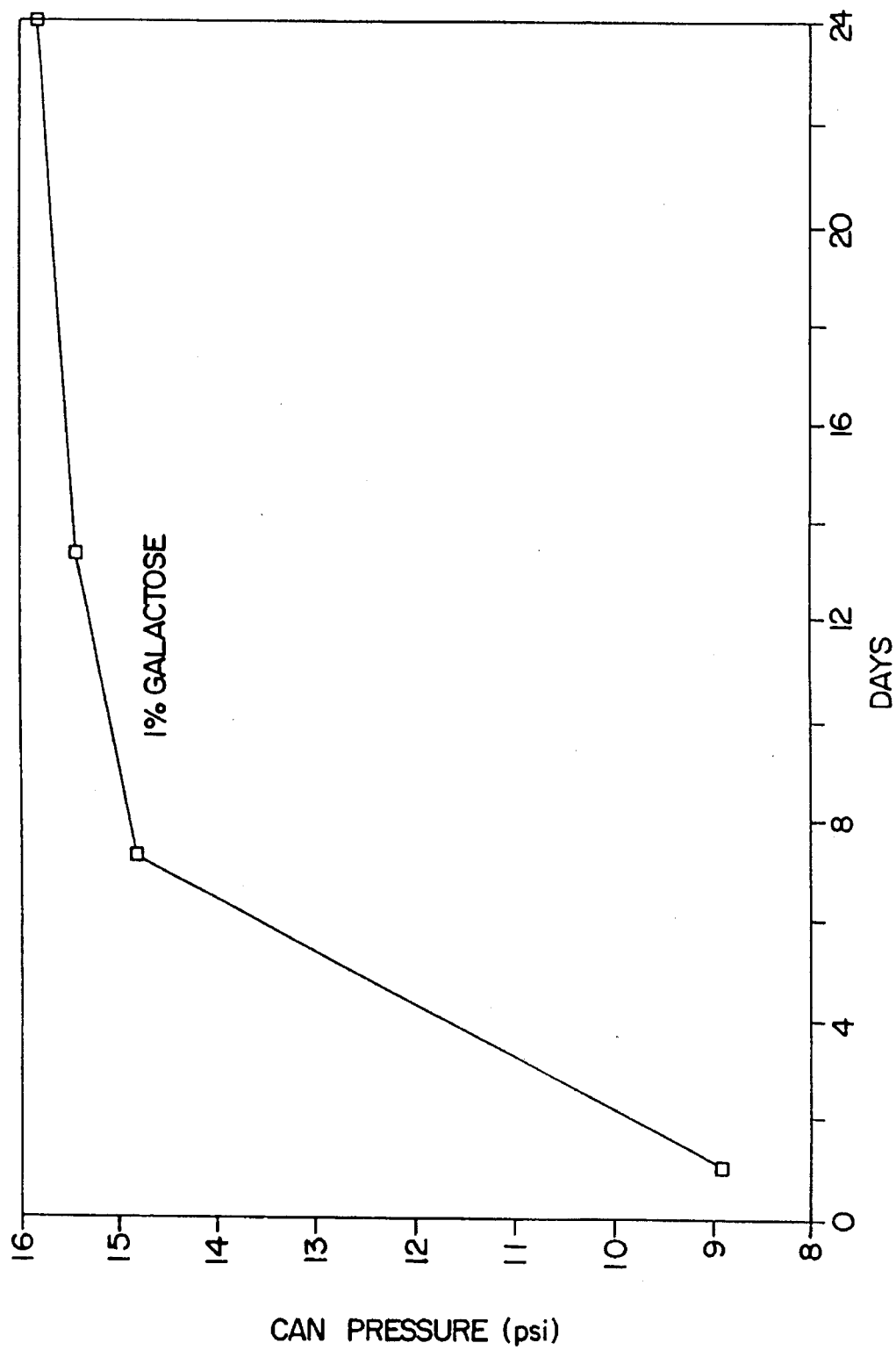

FIGS. 8 and 9 illustrate the can pressures of the samples as a function of time, with the can pressures for samples from each batch being averaged together to generate these plots. It can be seen that the ultimate can pressure of the sample is generally proportional to the amount of galactose in the dough. Whereas the sample containing 0.63 wt. % galactose had a can pressure of about 5–6.5 psi, the 0.75 wt. % dough had can pressures of about 9–10.5 and the pressure in the dough with 3 wt. % yeast and 1 wt. % galactose generated a maximum pressure of just under 16 psi. Accordingly, it appears as though the desired pressure in a container of the invention can be fairly readily controlled as a simple function of the amount of galactose added to the dough—once the galactose is exhausted, the dough will substantially cease producing carbon dioxide.

EXAMPLE 6

The D308.3 yeast perhaps adversely affected the sensory appeal of baked doughs containing such yeast in that the final baked product exhibited a slightly off-white color. Although all of the other organoleptic qualities of the dough were exemplary, doughs which would not exhibit this slight discoloration would probably be more appealing to consumers. It was determined that the discoloration of the dough was most likely due to inability of the D308.3 yeast to make adenine, causing the yeast to develop a pinkish or reddish hue when it is grown in a medium without adenine supplementation. This discoloration of the yeast is presumed attributable to a build up of metabolites which are toxic to the yeast (but not to humans).

Spontaneous revertant strains of the D308.3 yeast which do not require adenine for metabolization, referred to herein as RD308.3 yeast, were isolated. First, a concentrated paste of the D308.3 yeast was formed by spinning down the yeast in a rotor, as outlined in Example 2. This yeast paste was then diluted with a potassium phosphate monobasic buffer (about 43 mg $KH_2PO_4$ added to a liter of distilled water, with the Ph adjusted to about 7.2 with NaOH) and spread on an "adenine drop out" (ADO) medium, i.e. a medium which does not contain any supplemental adenine, at a concentration of about $1 \times 10^7$ colony forming units (CFU)/ml. The ADO medium contained, for each liter of distilled water, about: 6.7 g of bacto-yeast nitrogen base without amino acids, 20 g galactose, and 20 g of bacto-agar, 2 g of a "drop out mix" which contained alanine, argenine, asparagine, aspartic acid, cysteine, glutamine, glutamic acid, glycine, histidine, inositol, isoleucine, leucine, lysine, methionine, para-aminobenzoic acid, phenylalanine, proline, serine, threonine, tryptophan, tyrosine, uracil, and valine. (Substantially the same formula is taught by Rose et al. in Appendix A of *Methods in Yeast Genetics, A Laboratory Course Manual* (1990), which is incorporated herein by reference, at pages 179–180, but that formula used glucose rather than galactose.)

These ADO plates were incubated at about 25° C. for approximately 4 days and colonies of the yeast which did not require adenine were isolated. Identifying these colonies was greatly simplified by the fact that the non-revertant strains tended to be pinkish or reddish in hue while the revertant colonies were whitish. The isolated yeast was then once again plated onto a fresh ADO medium and incubated under substantially the same conditions. Colonies of revertant strains of the yeast were once again isolated from any strains inadvertently carded over in the first isolation and the platting and incubation were repeated one final time. Although it is believed that one skilled in the art could readily make such a yeast in light of the present disclosure, this resulting strain of RD308.3 yeast has been deposited with the ATCC on 5 Mar. 1993, under number ATCC 74212 and this strain is available to the public from the ATCC.

Two samples were prepared, with one sample containing the original D308.3 yeast and the other containing the RD308.3 yeast. These samples were prepared by mixing an isolated colony (about one loop) of the desired yeast with about 5 ml of YEP/galactose (which contained about 10 g of bacto-yeast extract, 20 g of bacto-peptone, and about 20 g of galactose per 1 liter of distilled water) and incubating for about 12–15 hours at about 30° C. (The formula for the YEP/galactose medium is substantially the same as the YEP/glucose formula taught on page 177 of Appendix A of *Methods in Yeast Genetics*, noted above, except that the glucose in that formula was replaced with galactose in the present medium.) Titer results indicated a population of approximately $48 \pm 2 \times 10^5$ CFU/ml for each strain. For each of the resulting samples, about 100 µl of the sample was added to three separate 5 ml potions of media, with one medium comprising just YEP, another comprising YEP and glucose and the third comprising YEP and galactose.

Figure 10:
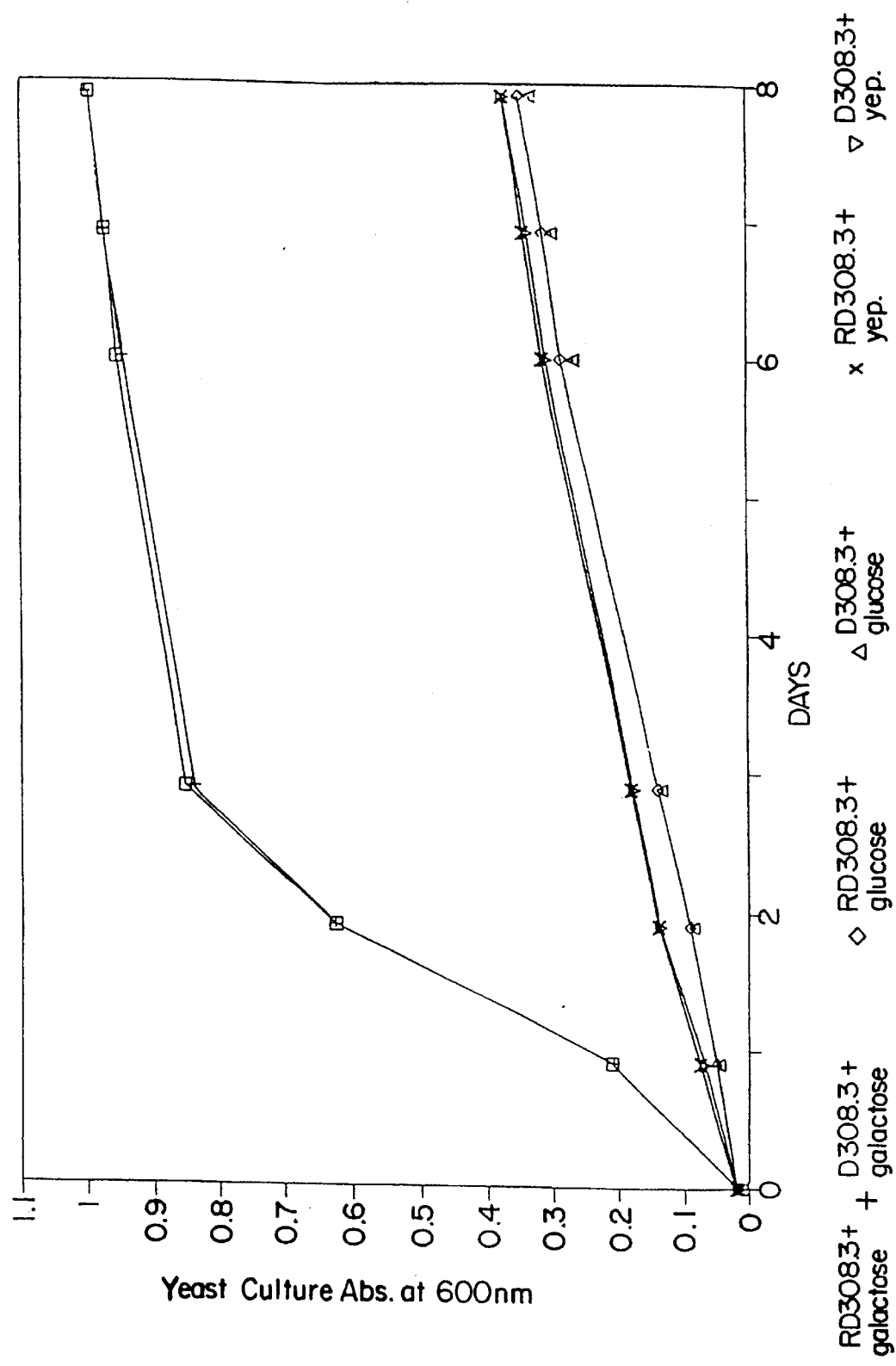
FIG. 10 depicts the growth of D308.3 and RD308.3 yeast on three different media as a function of absorbance.

The absorbance of each resulting sample was measured over time and is graphically illustrated in FIG. 10. The growth behavior of the D308.3 and RD308.3 yeasts appeared to be essentially the same for all three of these growth media. Furthermore, both of these yeasts appear able to readily metabolize galactose, but can only grow slightly on YEP or YEP/glucose. It is also interesting to note that both the D308.3 strain and the RD308.3 strain grew slightly less on the YEP/glucose than on YEP alone. This further demonstrates the substantial inability of these yeasts to metabolize glucose.

The auxotrophic markers adenine, histidine, methionine and tryptophan as growth supplements for the D308.3 and RD 308.3 strains were compared by standard techniques. The D308.3 yeast was not able to grow on galactose minimal media unless all four of these growth supplements were present, but the RD 308.3 yeast was able to grow if only the histidine, methionine and tryptophan were added.

Thus, the only significant difference noted between the auxotrophic markers of these two strains was that the D308.3 yeast requires adenine supplementation while the RD308.3 yeast does not. Accordingly, it is believed that the RD308.3 yeast will behave substantially as described above in connection with the D308.3 yeast when added to dough, but the slight discoloration of baked goods associated with doughs containing the D308.3 yeast should be substantially eliminated.

Figure 11:
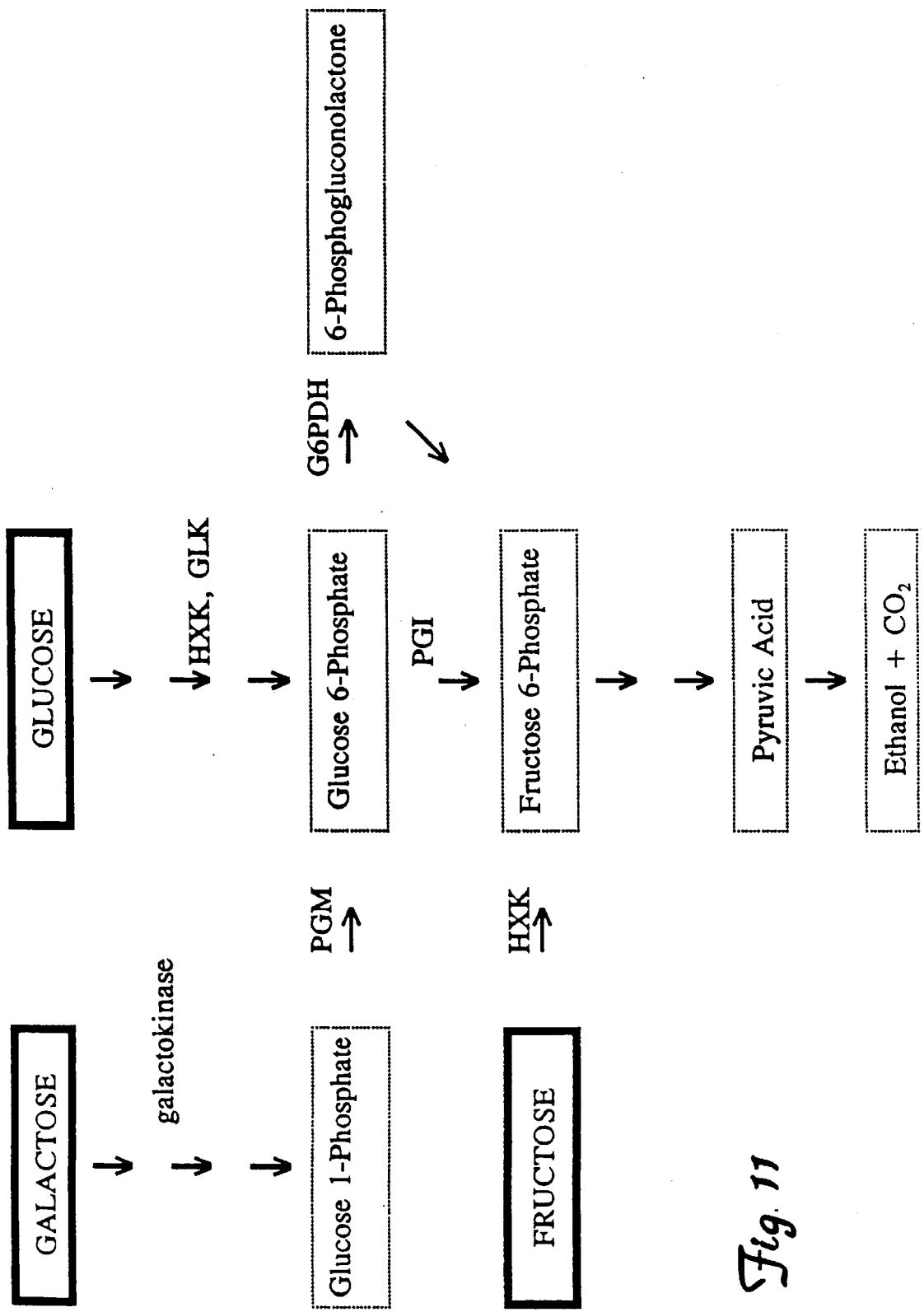
FIG. 11 is a schematic representation of the process of glycolysis, showing the reaction pathways for the utilization of various sugars in fermentation.

FIG. 11 is a schematic representation of the process of glycolysis. As is well known in the art, various sugars are broken down by glycolysis into pyruvic acid via glycolysis and the resulting pyrovic acid can be utilized by yeast to generate carbon dioxide through fermentation in an anaerobic environment.

As schematically illustrated in FIG. 11, glucose can be converted into glucose 6-phosphate by either hexokinase (HXK) or glucokinase (GLK). This glucose 6-phosphate can then be converted into fructose 6-phosphate by one of two pathways. In the normal glycolytic pathway, glucose 6-phosphate is converted into fructose 6-phosphate by the action of phosphoglucoisomerase.

In an alternative pathway for converting glucose 6-phosphate to fructose 6-phosphate, the glucose 6-phosphate is first converted into 6-phosphogluconolactone by the action of glucose 6-phosphate dehydrogenase (G6PDH), also known as zwischenferment (ZWF). Through the pentose phosphate pathway, also called the pentose phosphate shunt, this 6-phosphogluconolactone can be converted into fructose 6-phosphate.

In the embodiment described above wherein the yeast is substantially incapable of fermenting any sugars native to the dough systems, the yeast mutation was substantially incapable of generating either hexokinase (HXK) or glucokinase (GLK). As can be seen from the schematic illustration of FIG. 11A, this prevents glucose or fructose from being converted into fructose 6-phosphate. Since the yeast is substantially incapable of converting either glucose or fructose into fructose 6-phosphate, glucose and fructose generally cannot be converted into pyruvic acid and therefore cannot be utilized effectively by the yeast to produce $CO_2$.

Figure 11A:
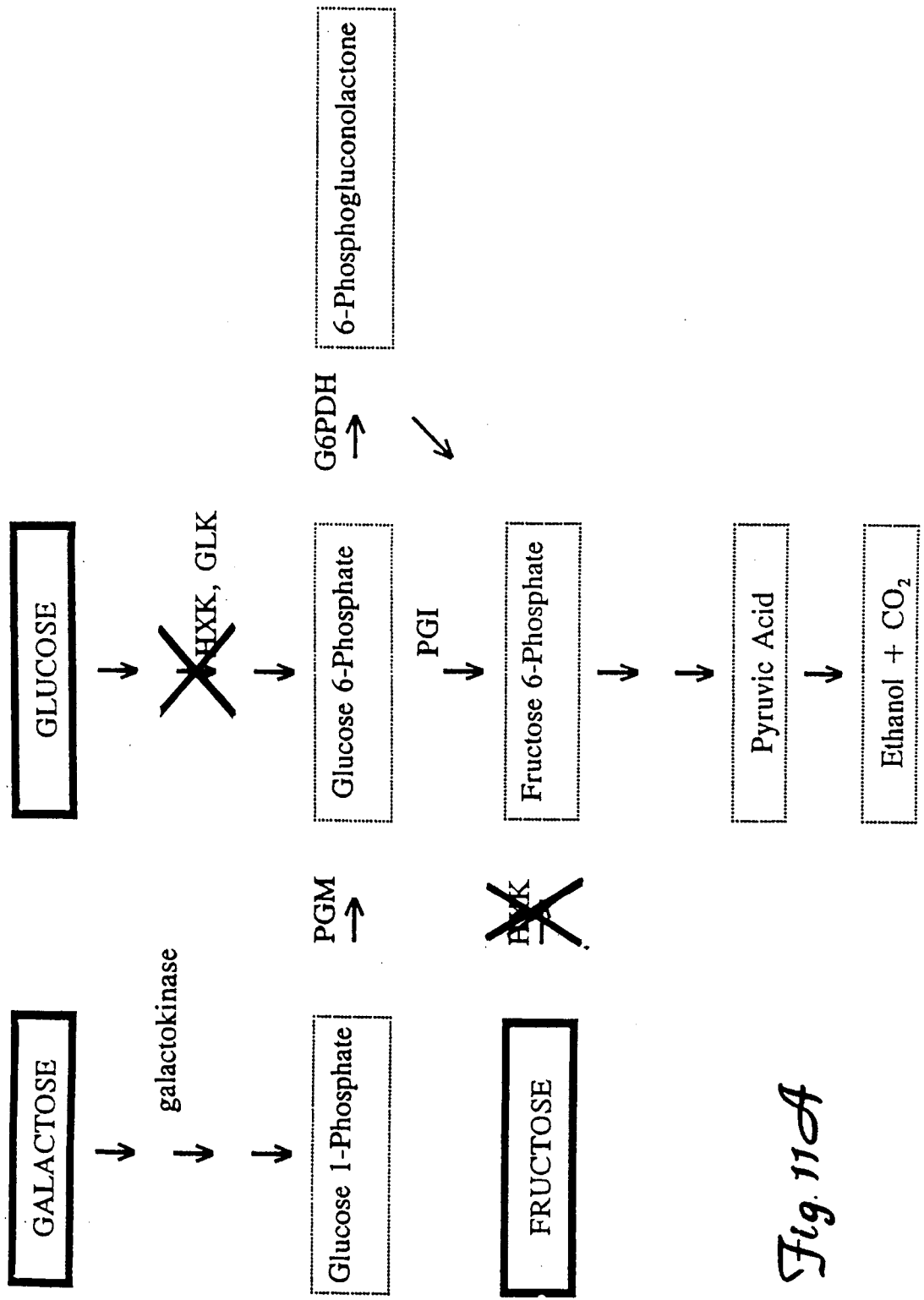
FIG. 11A is a schematic representation of the process of glycolysis, showing the reaction pathways for the utilization of various sugars in fermentation, wherein inactivated enzymes are shown with an 'x'.
Figure 11:
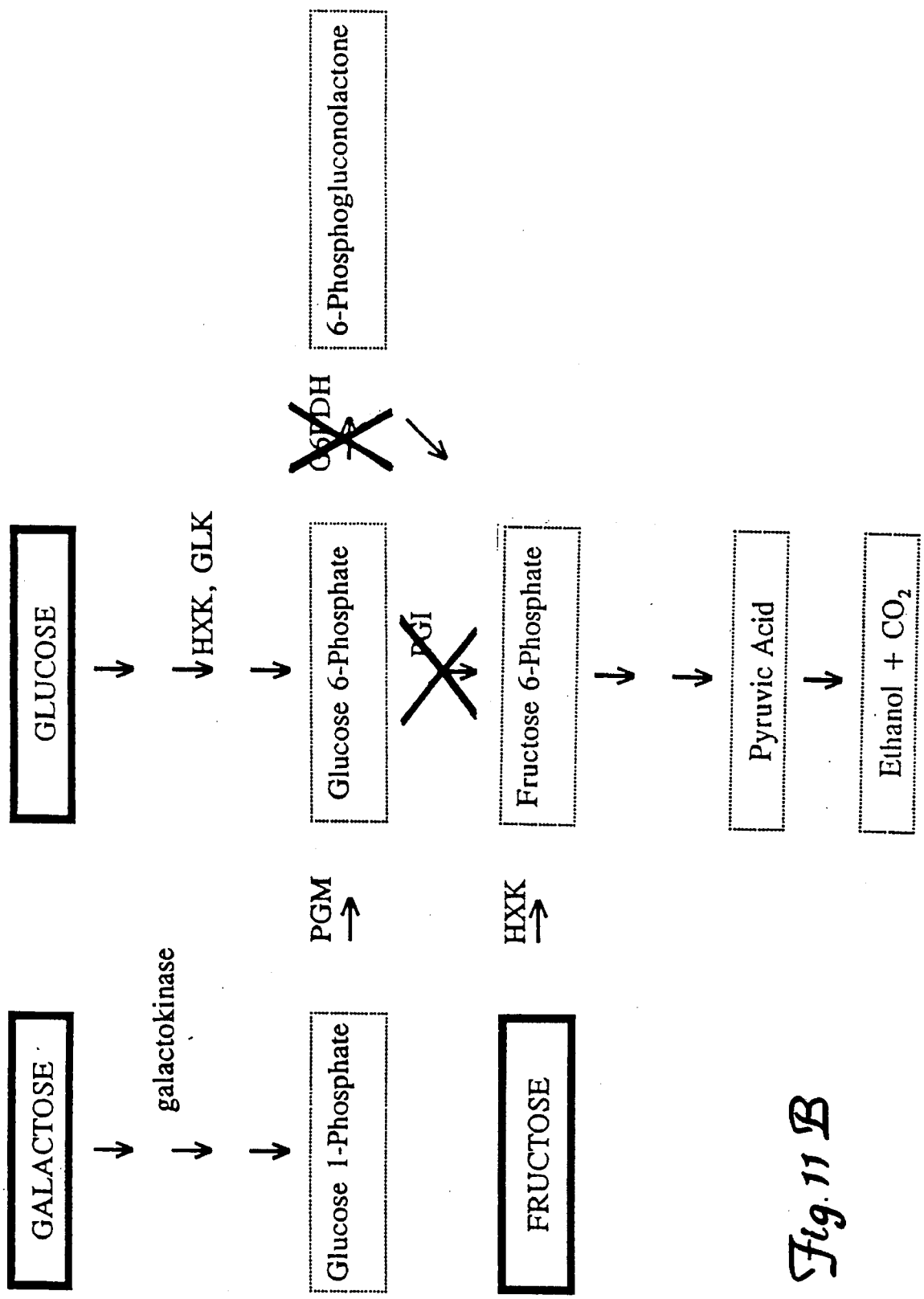

As can be seen in the schematic representation of FIG. 11A, galactose can be converted into glucose 1-phosphate by the action of galactokinase. This glucose 1-phosphate can then be converted into glucose 6-phosphate through the action of phosphoglucomutase. This glucose 6-phosphate can then be converted into fructose 6-phosphate, and thence to pyrovic acid as outlined above, by either phosphoglucoisomerase (PGI) or glucose 6-phosphate dehydrogenase (G6PDH). Accordingly, the yeast in the embodiment set forth above can utilize galactose through the action of galactokinase, but the pathways for the glycolysis of glucose and fructose are disabled due to a lack of hexokinase and glucokinase.

As noted above, in an alternative embodiment, the present invention does not utilize a non-native sugar, but instead ferments a sugar which is native to the dough system, but is present only in a limited quantity. In one particularly preferred embodiment of this invention, the native sugar is fructose. Fructose is commonly present in wheat flours, but in a concentration of less than 0.1 wt. %, with concentrations on the order of 0.02–0.08 wt. % being common for most wheat flours. Once a wheat flour is I0 combined with water and yeast, this relatively low concentration of fructose will be diluted even further. As doughs leavened with haploid yeasts commonly require at least about 1.0 wt. % of a fermentable substrate to generate the 100–200 ml of $CO_2$ necessary to proof about 100 g of dough, the quantity of native fructose generally will be less than that necessary to adequately proof a dough.

In accordance with the present invention, a yeast which is capable of phosphorylating only selected sugars to produce fructose 6-phosphate is mixed with flour and water to form a dough composition. In one preferred embodiment, the yeast is capable of fermenting fructose but is substantially incapable of fermenting any sugar naturally occurring in the flour in significant concentrations. An additional quantity of fructose is added to the dough composition to provide additional fermentable substrate for the yeast. The quantity of fructose added to the dough should be sufficient to allow the yeast to generate about 100–200 ml $CO_2$/100 g of dough as measured at about 30° C. The amount of fructose necessary to generate these quantities of carbon dioxide should be determined on a case-by-case basis for different strains of yeast to yield the desired degree of proofing.

As described above and illustrated in FIG. 11, fructose requires hexokinase in order to be converted into fructose 6-phosphate through phosphorylation. Accordingly, the yeast used in accordance with the present invention must be capable of generating hexokinase. However, hexokinase also breaks glucose down into glucose 6-phosphate, which can then be converted into fructose by either PGI or G6PDH. In order to allow the yeast of the present invention to utilize fructose but not glucose, the two pathways for the conversion of glucose 6-phosphate into fructose 6-phosphate are blocked.

AS schematically depicted in FIG. 11B, this is accomplished in accordance with the instant invention by using a yeast which is both phosphoglucoisomerase negative ("PGI-") and glucose 6-phosphate dehydrogenase negative ("G6PDH-"), i.e. the yeast lacks PGI and G6PDH. As such a yeast cannot generate either PGI or G6PDH, it is substantially incapable of utilizing glucose 6-phosphate by converting it into fructose 6-phosphate by phosphorylation. Accordingly, even if glucose is converted to glucose 6-phosphate by the action of hexokinase or glucokinase, the process of glycolysis is substantially blocked at that point and the glucose cannot be converted to pyrovic acid.

As illustrated schematically in FIG. 11B, this leaves only one pathway through the glycolysis process, that being the conversion of fructose to fructose 6-phosphate by hexokinase. Thus, the mount of fructose in a dough of the present invention will determine the volume of carbon dioxide which is generated.

In accordance with one embodiment of the present invention, a yeast which is both PGI- and G6PDH- is mixed with flour, water and an mount of fructose sufficient to provide the desired degree of proofing of the dough. The mount of fructose added to the dough is optionally selected to produce a volume of 100–200 ml $CO_2$/100 g of dough as this is usually considered necessary to proof the dough, as noted above. The precise mount of fructose added to the dough will depend on a number of factors, including the specific strain of yeast being used and the amount of native fructose in the flour. Accordingly, the amount of fructose added to a given dough composition should be determined on a case-by-case basis for different dough formulations. However, once a suitable formula has been determined for a given composition, the volume of carbon dioxide produced can be predictably varied as a function of the mount of fructose added to the dough.

Although there do not appear to be any PGI-/G6PDH- yeasts currently commercially available, a skilled artisan in the field will be able to make such a yeast using known techniques, such as those outlined by Sherman et al., supra. In making such a yeast, one can cross a PGI- yeast with a G6PDH- yeast through known techniques.

Once the two yeasts have been crossed and sporulated to yield haploid strains, the strains should be tested to ensure that they are indeed PGI-/G6PDH-, i.e. they behave as though they have substantially no phosphoglucose isomerase and substantially no glucose 6-phosphate dehydrogenase activity. Once the PGI-/G6PDH- nature of the yeast is confirmed (e.g. by confirming substantially zero growth on glucose media)-, the yeast can be use to make a dough of the invention. For example, PGI-/G6PDH- yeast of the invention was made as follows.

EXAMPLE 7

A number of putatively PGI- yeast strains and a number of putatively G6PDH- yeast strains were obtained from publicly available sources. In this experiment, the following strains of *Saccharomyces cerevisiae* yeast were used:

| Yeast Strain | Genotype |
|---|---|
| N543-9D | α pgi1 leu2 can$^r$ cyh$^r$ SUC2 mal mel gal2 CUP1 |
| N548-8A | a pgk1 leu2 can$^r$ cyh$^r$ SUC2 mal mel gal2 CUP1 |
| 9520T4C | α pgi1 ade1 trp1 ura3 his2 metl4 |
| YM3269 | a zwf1 URA3 ura3-52 his3-200 ade2-101 lys2-801 try1-501 met- |

The YM3269 yeast's genotype includes the designation zwf1, indicating that the yeast is deficient in ZWF, i.e. glucose 6-phosphate dehydrogenase (G6PDH). The first three strains of yeast were all obtained from the YGSC at UC Berkeley, noted above; the last strain CYM3269) was obtained from Dr. M. Johnston, Department of Genetics, Washington University School of Medicine, St. Louis, Mo., USA. Although these particular yeast strains were selected for the present experiment, it is well within the ability of those skilled in the art to select or develop other suitable PGI- and G6PDH- strains of yeast. For instance, in "Identification of the Structural Gene for Glucose-6-phosphate Dehydrogenase in Yeast. Inactivation Leads to a Nutritional Requirement for Organic Sulfur", *The EMBO Journal*, vol. 10 no. 3 pp. 547–553 (1991), the teachings of which are incorporated herein by reference, Thomas et al. teach that a defect in the MET19 gene of *S. Cerevisiae* will cause such a yeast to be G6PDH- because the MET19 gene encodes glucose-6-phosphate dehydrogenase from yeast. Thomas et al. also describe methods by which such a defect can be cloned into other yeast strains.

The ability of each of these yeasts to utilize different substrates was tested by inoculating a sample of each of a number of different media with a sample of each yeast and measuring the absorbance of the samples over time at 25° C. The different media were all employed liquid YEP as a base and varied in the addition of sugars to the media, with one medium having no additional substrate, a second including glucose, a third including fructose, a fourth including sucrose, and a fifth including maltose. This process of testing the ability of yeast to grow on different media is well known in the art and need not be discussed in great detail here.

By using such known testing protocols, it was determined that the N543–9D yeast grew readily on fructose, sucrose and glucose but not on maltose. The ability of this yeast to grow on glucose indicates that it is not actually PGI-, as reported.

The 9520T4C. yeast strain also grew readily on fructose and sucrose, but grew poorly on maltose and initially could not grow well on glucose. After about 6 days of incubation in liquid glucose media, this strain did adapt to growth on glucose, though. It has been surmised that this strain is most likely at least partially PGI-, but that the yeast may be able to process glucose by shunting the glucose through the pentose phosphate pathway (noted above in connection with FIGS. 11) or the PGI- mutation may be "leaky", i.e. PGI is not fully disabled.

Strain YM3269 was able to grow readily on glucose, fructose and sucrose, although the yeast seemed to have difficulty growing on maltose. As can be seen in FIGS. 11, one would expect the yeast to be able to use glucose, fructose and sucrose despite a lack of G6PDH because the glucose 6-phosphate can proceed through the normal glycolysis pathway without having to go through the pentose phosphate pathway disabled by the lack of G6PDH.

The N54808A yeast grew slowly on glucose, fructose and sucrose and was generally unable to grow on maltose. This is consistent with an understanding from the literature that this yeast has a "leaky" phosphoglucokinase (PGK) mutation.

Thus, the YM3269 yeast was apparently G6PDH negative and the 9520T4C. yeast appeared to be PGI negative. Accordingly, these two yeast strains were selected for crossing to yield PGI-/G6PDH- haploids. In mating these two strains to make the desired haploids, a protocol was derived from *Methods in Yeast Genetics, A Laboratory Course Manual*, Cold Spring Harbor Laboratory Press, pp. 53–59 (1990), the teachings of which are incorporated herein by reference.

In accordance with this method, YM3269 yeast and 9520T4C. yeast were plated onto separate YEP+fructose plates using a sterile loop to apply the strains on their respective plates in a series of parallel lines about 7 mm apart. These plates were allowed to incubate at approximately 30° C. for about one day.

An impression of the G6PDH- YM3269 strain was made on a replicate plate pad. This impression was imprinted onto a fresh plate including a YEP+fructose medium (about 1 wt. % bacto-yeast extract, about 2 wt. % bacto-peptone, about 2 wt. % bacto agar, and about 2 wt. % fructose, with the balance being distilled water) supplemented with adenine, histidine, methionine and uracil. Using a fresh replicate plate pad, an impression of the 9520T4C. PGI- strain was made. The second replicate pad was imprinted on the same YEP+fructose plate used for the previous imprinting, but at an orientation generally perpendicular to the first imprint, resulting in a pattern of yeast strains resembling a checkerboard. This doubly imprinted YEP+fructose plate was incubated at approximately 30° C. overnight (i.e about 12–15 hours).

The YEP+fructose plate thus prepared was imprinted on a fructose minimal media plate containing adenine, histidine, methionine and uracil. The fructose minimal media included about 6.7 g of bacto-yeast nitrogen base without amino acids, about 20 g of bacto-agar and about 20 g of fructose in about 1 liter of distilled water; the adenine, histidine, methionine and uracil were added to this formula in aqueous form. Such a minimal medium, utilizing dextrose instead of fructose, as well as the formulas for the supplements are taught in *Methods in Yeast Genetics, A Laboratory Course Manual,* Cold Spring Harbor Laboratory Press, pp. 178–179 (1990), the teachings of which are incorporated herein by reference.

These fructose minimal media plates were incubated for about two days at about 30° C. Growth at the intersections of the "checkerboard" pattern was scored and plated onto a fresh fructose minimal media plate to isolate the diploid (crossed) colonies from the haploid colonies. The diploid colonies isolated on the fructose minimal media plate were streaked onto a plate of sporulation media and incubated for about 4–5 days at about 25° C. The sporulation media contained about 10 g (1 wt. %) potassium acetate, about 1.0 g (0.1 wt. %) bacto-yeast extract, about 0.5 g (0.05 wt. %) fructose, about 20 g (2.0 wt. %) bacto-agar, with the balance being about 1000 ml distilled water.

About one loopful of yeast cells was taken from the sporulation plate and combined with about 300 microliters distilled water and approximately 15 microliters glusulase in an Eppendorf™ microfuge tube. This solution was mixed by vortex and incubated at around 30° C. for approximately 30 minutes. The incubated sample was briefly sonicated to separate spore clusters. Within about 20 minutes of being made, serial dilutions of about $10^{-4}$, $10^{-5}$ and $10^{-6}$ of the sonicated sample were plated onto YEP+fructose plates.

These serial dilutions were then exposed to ethyl ether fumes in a manner adapted from "Guide to Yeast Genetics and Molecular Biology", Guthrie and Fink editors, in *Methods of Enzymology,* vol. 194, pp. 146–147 (1991), the teachings of which are incorporated herein by reference. In this process, a 4 mm×4 mm piece of filter paper was placed into the inverted lid of each petri dish containing one of the serial dilutions. In a ventilated hood, 0.75 ml of ethyl ether was added to each filter paper and the lids and dilutions were placed in a glass chamber along with a beaker containing 10 ml of ethyl ether to maintain the vapor pressure in the chamber elevated.

The chamber was sealed and the samples were incubated for about 15 minutes at room temperature, at which time an additional 0.75 ml portion of ethyl ether was added to each filter paper square. These samples were again incubated in the glass chamber at room temperature for about 15 minutes, following which the samples were removed from the chamber and allowed to sit in the open atmosphere with the lid of each sample ajar for about 30 minutes.

Isolated yeast colonies from each of the $10^{-4}$, $10^{-5}$ and $10^{-6}$ dilution plates and a sample of each of the YM3269 and 9520T4C parent strains were grid plated onto YEP+fructose plates and incubated at about 25° C. for approximately 24 hours. Each of these samples was then replicate plated onto one plate of YEP+fructose and one plate of YEP+glucose. These plates were then incubated at about 30° C. for about 1–2 days to determine which of the isolated putative YM3269×9520T4C strains were able to grow on the fructose-enriched medium but not the glucose-containing medium.

The growth rate of each isolated strain was then evaluated by inoculating a 5ml volume of YEP+fructose with one loop of the yeast. Control samples for each of the YM3269 and 9520T4C parent strains were also prepared by inoculating similar media with a loop of the parent yeast. These samples were incubated at about 30° C. for about 24 hours and 100 microliter samples of each resultant yeast were used to inoculate separate 5 ml samples of YEP, YEP+fructose and YEP+glucose, with one such set of three samples being prepared from each isolated strain and each of the parent strains. The absorbency of each sample was measured at 600 nm and the samples were incubated at about 25° C. for about 2 weeks, with absorbency measurements being taken about twice a week for each sample.

Approximately 200 colonies of putative YM3269×9520T4C haploid strains were initially obtained from the "checkerboard" plating. Of these 200 colonies 47 were found to grow on the fructose medium but substantially unable to grow on the YEP or YEP+glucose media in the initial stages of the incubation. As noted above, though, the 9520T4C parent strain was found to be able to adapt to the glucose media after about 6 days in incubation. Of the 47 strains which did not initially grow in the glucose medium, all but 15 demonstrated an ability to adapt to the glucose like the parent yeast. Accordingly, only 15 of the 200 initially isolated colonies were evaluated as being truly PGI-/G6PDH- in that they were able to grow on fructose but not on glucose. These 15 colonies are referred to herein as PGI-/G6PDH- 1 through PGI-/G6PDH- 15.

This experimental example therefore readily provided some 15 colonies of yeast which appear to be useful in the present invention. Although this experimental example illustrates one straightforward method of making yeast of the present invention, it is to be understood that other variations of this method or other procedures for making such yeasts will be apparent to those skilled in this field.

The PGI-/G6PDH- 1 yeast was deposited with the ATCC on Jul. 2, 1993 under designation number ATCC 74230. This strain has been deposited simply as an example of a suitable yeast strain in accordance with the invention; it is to be understood that any one or more of the 15 isolated PGI-/G6PDH- strains are believed likely to work as well as well and that other strains of yeast in accordance can be readily produced by those skilled in the art in accordance with the present disclosure.

In accordance with a further embodiment of the present invention, such a yeast of the invention is incorporated into a dough composition. In accordance with this embodiment, a yeast of the invention is mixed with flour, water and a substrate fermentable by the yeast. The substrate fermentable by the yeast may occur naturally in the dough system, but if so the quantity of such substrate in the dough should be no more than that necessary to generate 200 ml of $CO_2$ per 100 g of dough, and is desirably substantially less than that amount. As used herein, a substrate is said to be naturally occurring in the dough if it is either native to the flour or is generated over time by the action of enzymes in the flour on other carbohydrates initially present in the flour.

For instance, fructose occurs naturally in wheat and will generally comprise between about 0.02 wt. % and about 0.08 wt. % of wheat flour. Such fructose can be said to be native to the flour as it is present in the flour in its natural state. Wheat flours also include sucrose, which is a disaccharide of glucose and fructose, and sucrose can be broken down by the action of commonly occurring enzymes into its constituent monosaccharides, giving rise to additional fructose in the dough over time. The concentration of sucrose in most wheats is generally on the order of about 0.2 wt. %, which if completely broken down would yield approximately 0.1 wt. % additional fructose to the initial 0.02–0.08 wt. % fructose in the flour. Also, various wheat flour oligosaccharides (e.g. glucofructose) contain varying amounts of fructose which could possibly also contribute the total amount of fructose in a wheat flour dough system over time. Both the native fructose and that produced by the degradation of native sucrose and other native oligosaccharides is considered to be "naturally occurring" as that term is used herein.

Continuing with the example of fructose, it should be noted that the total naturally occurring fructose in most wheat flours will be no more than about 0.2 wt. %, even if the sucrose is completely degraded into glucose and fructose. By the time the flour is mixed with water and the other ingredients of the dough, the weight percentage of naturally occurring fructose in the dough composition will be even less, frequently on the order of about 0.12 wt. % of the dough. However, a concentration more on the order of 1 wt. % of a fermentable substrate is usually necessary to generate the 100–200 ml $CO_2$/100 g of dough necessary to adequately proof the dough. Accordingly, the naturally occurring fructose is substantially less than that which one would expect to be required to properly proof a dough made with the flour.

Fructose would therefore serve as a suitable substrate fermentable by yeast of the present invention, particularly where the yeast is to be used with wheat flours. Naturally occurring glucose, on the other hand, while initially present at relatively low concentrations in a refrigerated wheat flour dough (e.g. native concentrations on the order of about 0.2 wt. %) will, over time, increase in concentration to as much as 1 wt. % or more by the end of about 90 days of refrigerated storage. Thus, the "naturally occurring" glucose in wheat flour doughs can be as much or more than that necessary to suitably proof the dough.

Without further treatment of the wheat to limit the mount of naturally occurring glucose, the additional amount of glucose generated in the dough system over the anticipated 90-day shelf life of the product could very well generate more than the 100–200 ml of $CO_2$/100 g of dough desired for proper proofing of the dough. Furthermore, when dough is proofed in a standard container, the expansion of the dough during proofing is used to flush the container of air initially present in the container and to substantially seal the container. The mount of native glucose in wheat flours generally will not be sufficient to adequately flush and seal standard containers in commercial use today.

Inadequate flushing and sealing would permit some quantifies of air to remain in the container and, perhaps, enter the container before it is sealed. Significant oxygen concentrations in the container can have a number of adverse effects on the dough, such as graying of the dough and promoting growth of deleterious bacteria. Thus, the native glucose may be insufficient to generate the 15–20 psi internal pressure desired in dough packages, but yet the total volume of $CO_2$ generated in the dough from the total naturally occurring glucose may well exceed the desired volumes. Accordingly, glucose would not be a good candidate for a fermentable substrate for a yeast-leavened dough of the invention.

By utilizing a yeast which is capable of fermenting only a substrate (most commonly a sugar) which is present in the dough in naturally occurring amounts no more than that necessary to proof a dough, the total volume of carbon dioxide which the yeast can generate will also be limited. Hence, by selecting the concentration of fermentable substrate in the dough and using a yeast of the present invention, the proofing of a dough with yeast can be controlled on a commercial basis. This is critical, as outlined above, in that it can permit the dough to be stored for extended periods of time, e.g. on the order of 90 days or more, without rupturing the container in which it is placed.

EXAMPLE 8

In order to test the ability to use the yeast produced in Example 7 to proof a dough composition and to survive extended refrigerated storage, such a yeast was mixed with flour and water to form a dough. In particular, yeast strain PGI-/G6PDH- 1 (ATCC designation number ATCC 74230) was used in four different dough compositions, with each dough composition including about: 428.3 g (57.7 wt. %) wheat flour; 259.7 g (35.0 wt. %) distilled water; 26.5 g (3.56 wt. %) wheat gluten preblend of a formula substantially the same as outlined in Example 1; 5.63 g (0.76 wt. %) salt; and 15.0 g (2.02 wt. %) PGI-/G6PDH- 1 yeast. The four dough compositions differed in the amount and type of substrate added to the dough, with the first composition having no added sugars, the second having about 7.5 g (1.0 wt %) fructose, the third dough having about 7.5 g (1.0 wt %) glucose, and the fourth dough having about 7.5 g (1.0 wt %) sucrose.

The doughs were made by slurrying the PGI-/G6PDH- 1 yeast with the water and the sugar, if any, and mixing this slurry with the remaining ingredients in a table top Hobart mixer. The dough was mixed at speed 1 for about 30 seconds, followed by mixing at speed 2 for approximately 4 minutes.

Figure 12:
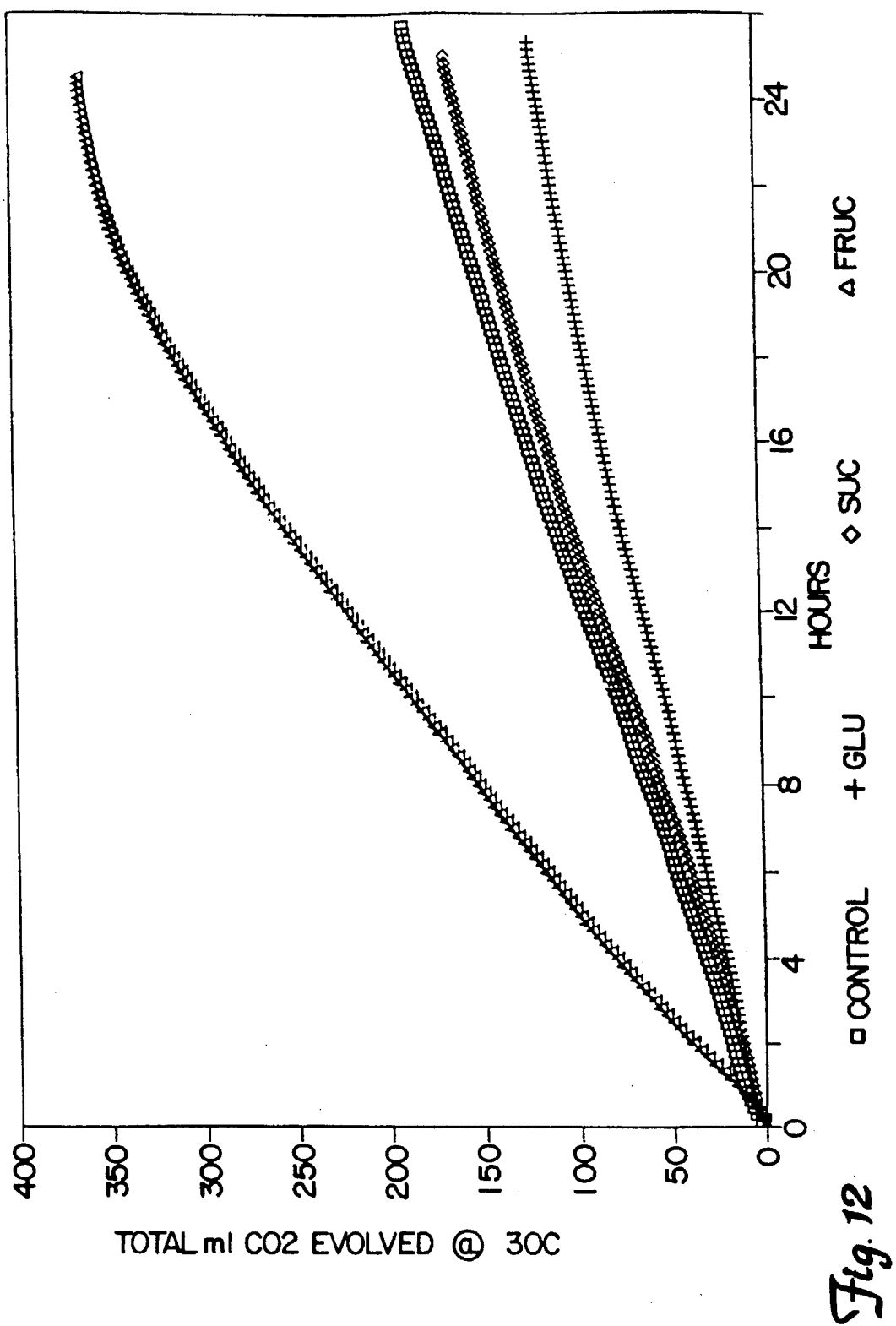
FIG. 12 is a graph showing the total volume of carbon dioxide generated by PGI-/G6PDH- yeast-leavened dough compositions containing different sugars.
Figure 19:
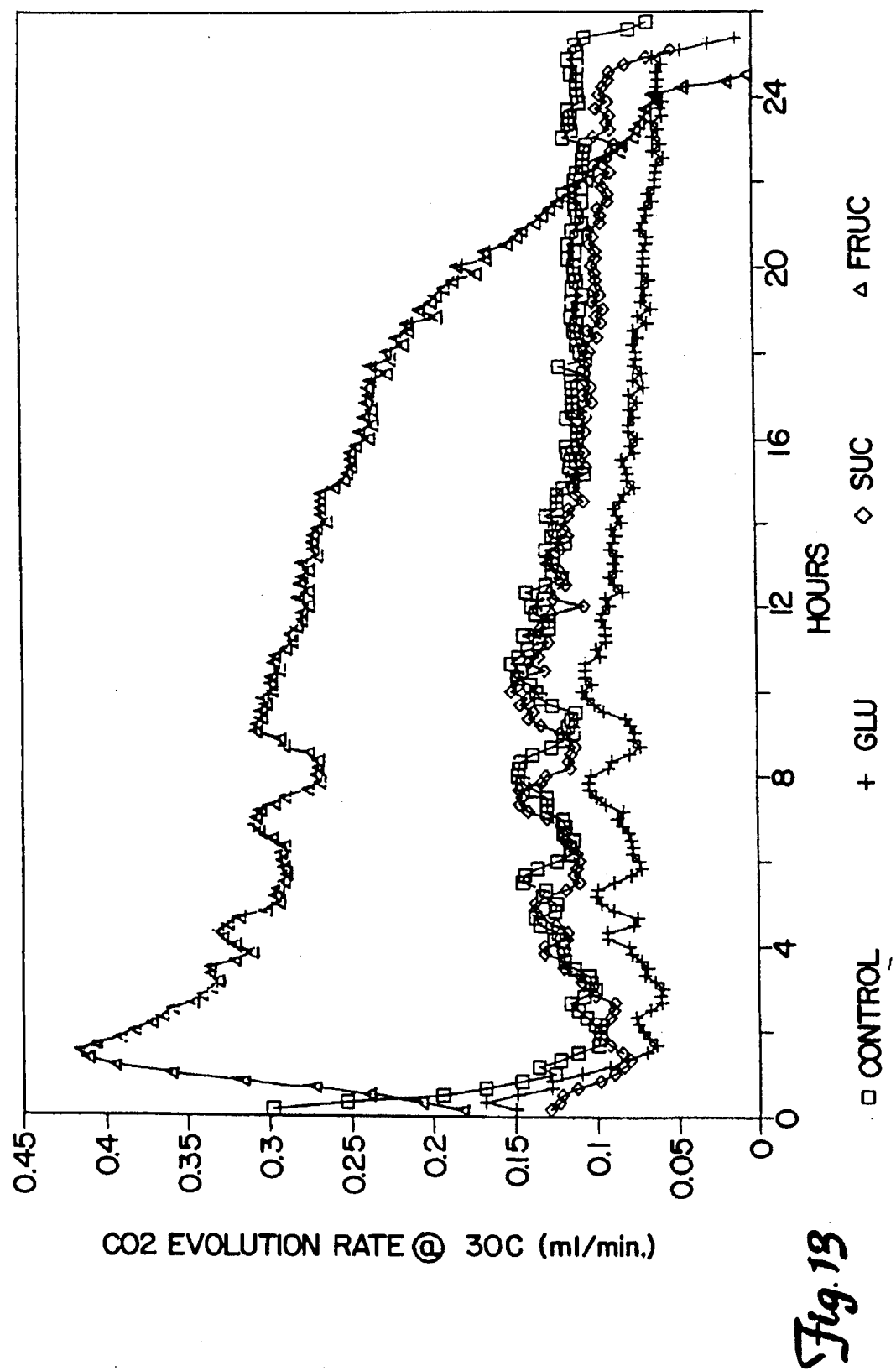

After the doughs were mixed, two 100 g samples of each dough composition were placed in separate Risograph sample jars. These sample jars were then held in the Risograph at about 30° C. for about 24 hours and the gas evolution of these samples was monitored by the Risograph. FIG. 12 is a graph of the total volume of $CO_2$ generated over time for each sample while FIG. 13 is a graph of the rate of $CO_2$ generation for the same samples. (The data collected from the two samples from each batch of dough was averaged together to yield the data for that sample shown in these drawings.)

Figure 14:
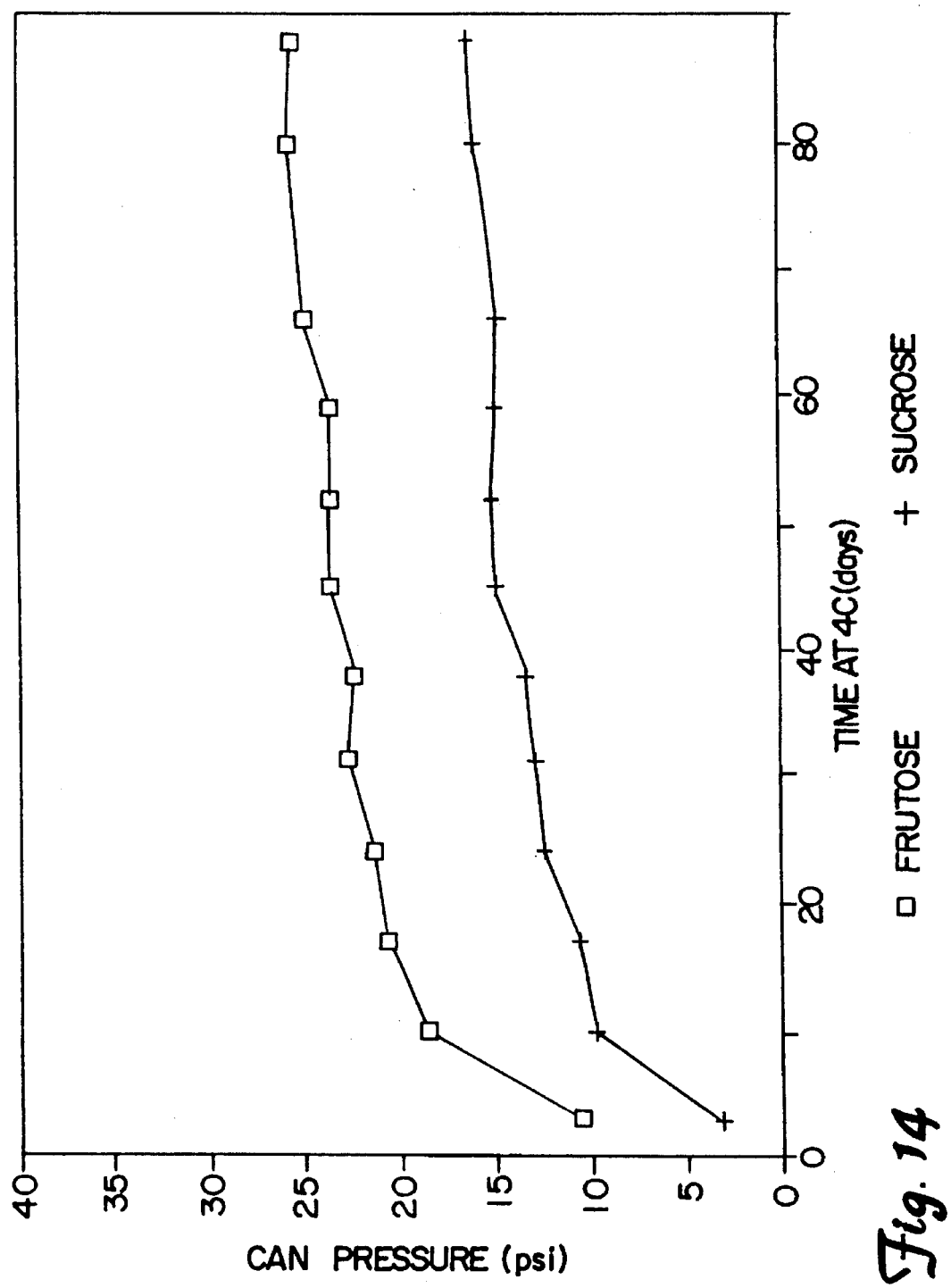
FIG. 14 plots measured can pressure over time for two dough compositions, one dough containing fructose and the other containing sucrose.

Additionally, two 210 g samples of each of the fructose-containing and sucrose-containing doughs were placed in standard, commercially available spirally wound cans (about 2.25" diameter by about 4" in length). The canned dough samples were then incubated at about 97° F. (36° C.) for about 3.5 hours and stored at about 4° C. for about 90 days. FIG. 14 is a graph of the pressure in the sealed container for each of these doughs over time. (The pressure measurements were begun after the initial proofing incubation at 97° F. and the data for the two samples of each dough were averaged together to yield the illustrated data for that dough.)

The data of FIGS. 12 and 13 indicate that the dough containing fructose generated significantly more $CO_2$ than the other three samples. This is much as one would expect for a dough leavened with a yeast which is both phosphoglucose isomerase (PGI) negative and glucose 6-phosphate dehydrogenase (G6PDH) negative. As illustrated in FIGS. 11 and 11B, such a yeast should be able to readily utilize fructose in the dough, but not other sugars.

The dough which did not include any additional sugar did generate some CO2, although it was substantially less than that generated by the fructose-supplemented dough. The yeast may have been able to utilize the naturally occurring fructose in the dough as a substrate in generating carbon dioxide. It is interesting to note that the 100 g control sample containing no non-naturally occurring fructose (i.e. no added fructose in the composition) generated somewhat more than 100 ml $CO_2$.

The reliability of this result is not certain, though. In some circumstances, various bacteria in a dough will generate $CO_2$ or other gases if the dough is proofed for an extended period of time, such as more than 10 hours. As the doughs of FIGS. 12 and 13 were held at about 30° C. for much longer than 10 hours, it is believed that at least some of the volume of gas generated by the control sample may be attributable to the action of bacteria, i.e. to a source other than the yeast. It is well known that the growth of bacteria in yeast can not only yield undesirable byproducts which can adversely affect the dough. Accordingly, commercially proofed doughs generally are proofed for as short a period of time as possible and one should not rely on the generation of $CO_2$ from sources other than the yeast in these doughs for leavening purposes.

Accordingly, it is believed that the volume of $CO_2$ generated by the yeast is less than 100 ml for this 100 g sample of dough. Since this falls below the level believed to adequately proof the dough, it appears as though the dough lacks sufficient naturally occurring fructose to proof the dough to the desired degree.

The dough containing 1 wt. % sucrose actually generated slightly less $CO_2$ than the control sample, which did not contain any additional sugars. At first, this may seem anomalous in that the additional sucrose could be broken down into glucose and fructose, adding to the fermentable substrate in the dough. This is not completely understood, but it is believed that this may be attributable either to an inability of the PGI-/G6PDH- 1 yeast to cleave sucrose into its constituent monosaccharides or to metabolic suppression of yeast due to the abundance of unconsumed glucose in the dough. The fact that the glucose-supplemented formulation produced even less gas than the sucrose dough would seem to bear out that the presence of glucose, which cannot by fermented by the yeast, is suppressing the metabolism of the yeast.

As noted above, FIG. 14 shows the pressure in the canned dough stability test. The fructose-supplemented dough reached an internal pressure of about 18 psi in the first 10 days of storage, with the pressure gradually creeping up to about 24 psi by the end of the 68 days. As explained above, it is desirable to have an internal can pressure of at least about 15–20 psi, but that the internal pressure of the can should not exceed about 40 psi or the container may rupture. Accordingly, the fructose-supplemented dough of FIG. 14 appears to readily meet the desired operational parameters of standard canned doughs and can be stored for extended periods of time without rupturing the container. In this case, the dough was stored for 90 days at refrigeration temperatures without any adverse effects on can pressure, which meets the requirements for most current commercially produce refrigeratable dough products, as noted above.

The sucrose-supplemented dough did not generate as much internal pressure as the fructose-supplemented dough. As seen in FIG. 14, the sucrose dough reached a pressure of less than about 10 psi in the first 10 days of refrigerated storage and gradually crept up to an internal pressure of about 14 psi by the end of the 68 days shown in this graph. It is interesting to note that this product did not reach the desired 15–20 psi of internal pressure even after more than two months of storage. Accordingly, by varying the concentration of non-fermentable sugar (e.g. glucose) in the dough product system, one can effectively limit or control the gas production of the dough, and hence internal pressure of a package containing the dough, during the dough's shelf fife.

Another embodiment of the present invention provides a method of forming a dough which can be stored at refrigeration temperatures for extended periods of time without generating significant volumes of carbon dioxide. This method may further include the steps of packaging the dough, proofing the dough in the package, and storing the dough for an extended period of time at refrigeration temperatures.

In making a dough of the invention, flour, water, a yeast substantially incapable of fermenting carbohydrates native to the flour, and a quantity of a carbohydrate fermentable by the yeast are mixed together, as outlined above. The amount of the fermentable carbohydrate added to the dough is desirably sufficient to provide only the necessary degree of proofing of the dough; adding too much fermentable substrate could cause adverse changes in dough rheology due to overfermentation. This amount is optimally determined on a case-by-case basis for a given strain of yeast as different strains of yeast may utilize the fermentable substrate more efficiently than others.

In a particularly preferred embodiment of the method of the invention, the yeast used in making the dough is a GAL+ yeast and a predetermined quantity of galactose is added to the dough to provide the desired degree of proofing. This GAL+ may be the D308.3 yeast or the RD308.3 yeast described above, but it is to be understood that other GAL+ yeasts can be made in accordance with the present disclosure which will also work in accordance with the invention.

As noted above, the method may further include the steps of packaging the dough, proofing the dough in the container, and storing the dough at refrigeration temperatures for an extended period of time. Virtually any known refrigeratable dough package known in the art may be used in this method. For instance, spirally wound dough containers such as those currently used in commercially manufactured refrigeratable dough products should suffice. A quantity of dough somewhat less than that necessary to fill the container is placed in the container, leaving a headspace in the container when it is sealed.

The dough may then be proofed in the container, expanding to fill the container and flush out any air in the headspace. The proofing is continued until substantially all of the fermentable carbohydrate is consumed by the yeast, at which point an internal pressure of about 15 to about 20 psi is attained in the container. This proofing may be advantageously carried out at an elevated temperature, e.g. about 30° C. to about 40° C., to allow the yeast to ferment, and thus proof the dough, more rapidly.

This proofed dough may then be placed in refrigerated storage for extended periods of time, desirably up to at least about two weeks. The dough of the invention is optimally capable of storage at refrigeration temperatures for at least about 90 days, the anticipated shelf life of current doughs, as explained above. By "refrigerated storage", storage at temperatures between about 12° C. and about 0° C., and preferably between about 4° and bout 7.2° C., is intended. Such temperatures are referred to in the present specification as "refrigeration temperatures".

While preferred embodiments of the present invention have been described, it should be understood that various changes, adaptations and modifications may be made therein without departing from the spirit of the invention and the scope of the appended claims.

What is claimed is:

1. A yeast-leavened refrigeratable dough product comprising flour, water and yeast, the yeast characterized by yeast deposited with the ATCC, Deposit No. 74230, wherein the yeast are capable of phosphorylating substantially only fructose to produce fructose-6-phosphate, the total amount of carbohydrate present in the dough being no more than necessary to produce about 200 ml $CO_2$/100 g of dough.

2. The dough product of claim 1 wherein the yeast is "capable" of fermenting fructose but is substantially incapable of fermenting glucose.

3. A yeast characterized by yeast deposited with the ATCC, Deposit No. 74230, capable of fermenting fructose but substantially incapable of fermenting any other sugar naturally occurring in wheat flour.

4. The yeast of claim 3 wherein said yeast is capable of fermenting fructose but is substantially incapable of fermenting glucose.

5. The yeast of claim 3 wherein said yeast is of the species Saccharomyces cerevisiae.

6. The yeast of claim 3 wherein said yeast is substantially phosphoglucose isomerase negative and substantially glucose 6-phosphate dehydrogenase negative.

* * * * *

UNITED STATES PATENT AND TRADEMARK OFFICE
CERTIFICATE OF CORRECTION

PATENT NO. : 5,571,544
DATED : November 5, 1996
INVENTOR(S) : David J. Domingues It is certified that error appears in the above-indentified patent and that said Letters Patent is hereby corrected as shown below:

Col. 1, Line 42, delete the word "rapture" and insert the word --rupture--;
Col. 1, Line 48, delete the word "rapture" and insert the word --rupture--;
Col. 1, Line 56, delete the word "lime" and insert the word --time--;
Col. 1, Line 57, delete the word "fife" and insert the word --life--;
Col. 1, Line 60, delete the word "rapture" and insert the word --rupture--;
Col. 4, Line 18, delete the word "mounts" and insert the word --amounts--;
Col. 6, Line 11, delete the word "lime" and insert the word --time--"

Col. 8, Line 51, delete the word "rams" and insert the word --rates--;
Col. 9, Line 41, delete the word "ram" and insert the word --rate--;
Col. 10, Line 5, delete the number "96" and insert the symbol --%--;
Col. 10, Line 7, delete the number "96" and insert the symbol --%--;
Col. 10, Line 25, delete the word "con mining" and insert the word --containing--;
Col. 11, Line 35, delete the ".", before the word "galactose";

Col. 13, Line 33, delete the word "pyrovic" and insert the word --pyruvic--;
Col. 14, Line 2, delete the word "pyrovic" and insert the word --pyruvic--;
Col. 14, Line 17, after the word "is", delete the letters "I0";
Col. 14, Line 51, delete the word "AS" and insert the word --As--;
Col. 14, Line 62, delete the word "pyrovic" and insert the word --pyruvic--;
Col. 14, Line 66, delete the word "mount" and insert the word --amount--;
Col. 15, Line 5, delete the word "mount" and insert the word --amount--;
Col. 15, Line 6, delete the word "mount" and insert the word --amount--;
Col. 15, Line 7, delete the word "optionally" and insert the word --optimally--;

UNITED STATES PATENT AND TRADEMARK OFFICE
CERTIFICATE OF CORRECTION

PATENT NO. : 5,571,544
DATED : November 5, 1996
INVENTOR(S) : David J. Domingues It is certified that error appears in the above-indentified patent and that said Letters Patent is hereby corrected as shown below:

Col. 15, Line 10, delete the word "mount" and insert the word --amount--;
Col. 15, Line 18, delete the word "mount" and insert the word --amount--;
Col. 15, Line 33, after the word "media)", delete the "-";
Col. 15, Line 56, delete "CYM3269)" and insert --(YM3269)--;
Col. 19, Lines 54 and 55, delete the word "quantifies" and insert the word --quantities--;
Col. 22, Line 8, delete the word "fife" and insert the word --life--.

Signed and Sealed this

Fifteenth Day of April, 1997

Attest:

BRUCE LEHMAN

Attesting Officer

Commissioner of Patents and Trademarks